United States Patent [19]
Pettersen et al.

[11] Patent Number: 6,166,074
[45] Date of Patent: Dec. 26, 2000

[54] PHARMACEUTICAL COMPOSITIONS

[75] Inventors: Erik Olai Pettersen, Oslo; Rolf Olaf Larsen, Langesund; John Michael Dornish, Bekkestua; Bernt Børretzen, Heistad; Reidar Oftebro, Hvalstad; Thomas Ramdahl, Eiksmarka; Vidar Moen, Skien, all of Norway

[73] Assignee: Norsk Hydro A.S., Oslo, Norway

[21] Appl. No.: 08/669,407

[22] PCT Filed: Jan. 3, 1995

[86] PCT No.: PCT/NO95/00003

§ 371 Date: Oct. 4, 1996

§ 102(e) Date: Oct. 4, 1996

[87] PCT Pub. No.: WO95/18607

PCT Pub. Date: Jul. 13, 1995

[30] Foreign Application Priority Data

Jan. 4, 1994 [GB] United Kingdom .................... 9400047

[51] Int. Cl.[7] ........................................ A01N 37/10
[52] U.S. Cl. .................... 514/533; 514/315; 514/357; 514/408; 514/423; 514/432; 514/438; 514/445; 514/447; 514/451; 514/460; 514/461; 514/471; 514/473; 514/529; 514/534; 514/545; 546/184; 546/190; 548/556; 548/570; 549/61; 549/62; 549/65; 549/66; 549/68; 549/78; 549/356; 549/421; 549/424; 549/474; 549/491; 549/497; 558/265; 558/266; 558/267; 558/268; 560/179; 560/187; 560/226; 562/512; 562/599; 564/123
[58] Field of Search ...................... 514/533, 534, 514/545, 529, 315, 357, 423, 408, 432, 438, 447, 445, 451, 460, 461, 471, 473; 549/136, 61, 62, 65, 66, 68, 78, 356, 427, 424, 474, 491, 497; 546/184, 190; 548/556, 570; 562/512, 599; 558/265, 266, 267, 268; 560/179, 187, 226; 564/123

[56] References Cited

U.S. PATENT DOCUMENTS 3,293,220 12/1966 Minami et al. ........................ 37/43
3,390,008 6/1968 Giller et al. ........................ 117/138.5
4,758,591 7/1988 Takita et al. ............................ 514/548
4,841,097 6/1989 Takita et al. ............................ 514/171
4,874,780 10/1989 Borretzen et al. ...................... 514/432
4,997,850 3/1991 Kimura et al. .......................... 514/544
5,149,820 9/1992 Borretzen et al. ...................... 548/215

FOREIGN PATENT DOCUMENTS 147174 7/1985 Japan .
395441 10/1990 Japan .
283139 9/1988 Norway .
552880 7/1993 Norway .

OTHER PUBLICATIONS

CA 93(22):210255, Setsuo et al., Dec. 01, 1980, abstract.

Kanwarpal et al., "Conversion of Aldehydes into Geminal Diacetates", J. Org. Chem. 1983, 48, pp. 1765–1767.

Freeman et al., "An Ionic Chain Mechanism for the Substitution of an Actetate Group by the 2–Nitropropan–2–ide Ion in Benzylidiene Diacetates", Aust. J. Chem., 1976, 29, pp. 327–337.

*Primary Examiner*—Dwyane C. Jones
*Attorney, Agent, or Firm*—Wenderoth, Lind & Ponack, L.L.P.

[57] ABSTRACT

Pharmaceutical compositions which are useful for the treatment of cancer or illnesses which arise due to an abnormally elevated cell proliferation comprise acyl derivatives of aromatic aldehydes, especially arylidene diesters and α-alkoxyarylidene esters of general formula (I).

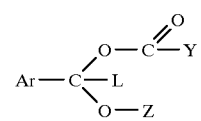

(I)

16 Claims, 12 Drawing Sheets

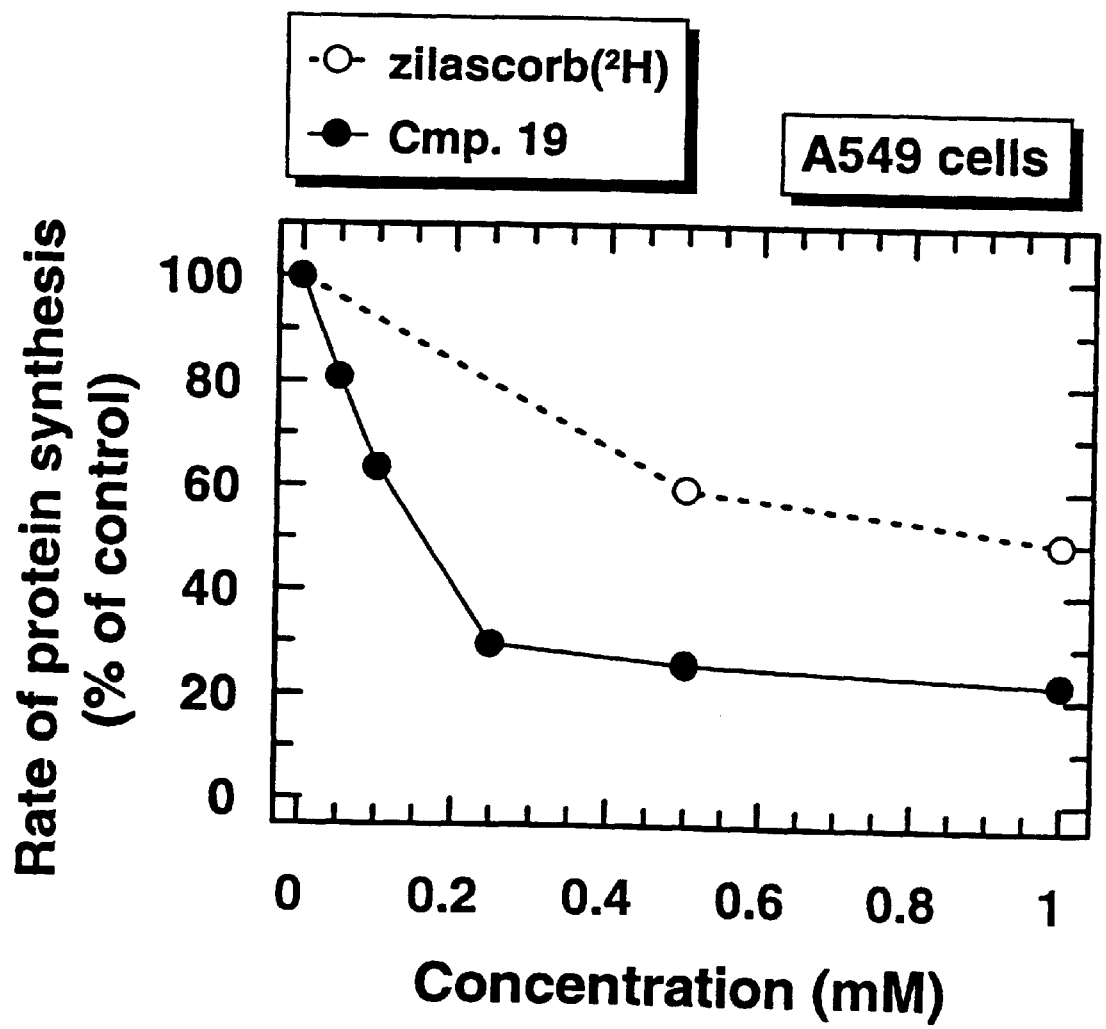

PHARMACEUTICAL COMPOSITIONS

BACKGROUND OF THE INVENTION

The present invention concerns pharmaceutical compositions which may be used in the treatment of cancer, especially carcinoma, or illnesses which arise due to an elevated cell proliferation. The compounds which are active in the compositions according to the present invention are acyl derivatives of aromatic aldehydes, especially arylidene diesters and alkoxyarylidene esters.

It is known from EP215395, J63264411, J88009490, J55069510 and EPO283139 that aromatic aldehydes and derivatives thereof have an anti-cancer effect. These compounds exert an inhibitory action on the protein synthesis of the cells.

In solid tumors this reduced protein synthesis may result in a lack of vital proteins which lead to cell death. In normal cells there is a potential capacity for protein synthesis which is higher than in most cancer cells of solid tumors. This is demonstrated by comparison of the cell cycle duration in normal stem cells, which is often below 10 h, with that of most cancer cells of solid tumors, which is typically 30–150 h (see Gavosto and Pileri in: *The Cell Cycle and Cancer*. Ed.: Baserga, Marcel Dekker Inc., N.Y. 1971, pp 99). Since cells, as an average, double their protein during a cell cycle, this means that protein accumulation is higher in growth-stimulated normal cells than in most types of cancer cells.

Keeping in mind this difference between normal and cancer cells, there is another difference of similar importance: while normal cells respond to growth-regulatory stimuli, cancer cells have a reduced or no such response. Thus, while normal cells, under ordinary growth conditions, may have a reserve growth potential, cancer cells have little or no such reserve. If a protein synthesis inhibition is imposed continuously over a long period of time on normal cells as well as on cancer cells it is probable that the two different types of cells will respond differently: Normal tissue may take into use some of its reserve growth potential and thereby maintain normal cell production. Cancer tissue however, have little or no such reserve. At the same time the rate of protein accumulation in most cancer cells is rather low (i.e. protein synthesis is only slightly greater than protein degradation). Therefore the protein synthesis inhibition may be just enough to render the tumor tissue imbalanced with respect to protein accumulation, giving as a result a negative balance for certain proteins. During continuous treatment for several days this will result in cell inactivation and necrosis in the tumor tissue while normal tissue is unharmed.

To date, the most tested compound inducing reversible protein synthesis inhibition and displaying anti-cancer activity is zilacorb($^2$H) [5,6-benzylidene-d$_1$-ascorbic acid]. The protein synthesis inhibiting activity of this prior art compound is described in detail by Pettersen et al. (Anticancer Res., 11: 1077–1082,1991) and in EP0283139. Zilacorb($^2$H) induces tumor necrosis in vivo in human tumor xenografts in nude mice (Pettersen et al., Br. J. Cancer, 67:650–656, 1993), and the compound is currently being tested in Phase I and Phase II clinical trials. Since zilascorb($^2$H) is a derivate of an aromatic aldehyde, the activity of new compounds described in the present invention will be compared with that of zilascorb($^2$H).

It is known from UK Patent application 9026080.3 that benzaldehyde compounds, previously known as anti-macer agents may be used for combatting diseases resulting from an abnormally elevated cell proliferation. Such compounds also exert an effect on cells having an abnormally elevated cellular proliferation rate, and accordingly the compounds may be used for the treatment of diseases such as psoriasis, inflammatory diseases, rheumatic diseases and allergic dermatologic reactions.

Dermatologic abnormalities such as psoriasis are often characterized by rapid turnover of the epidermis. While normal skin produces ca. 1250 new cells/day/cm$^2$ of skin consisting of about 27,000 cells, psoriatic skin produces 35,000 new cells/day/cm$^2$ from 52,000 cells. The cells involved in these diseases are however "normal" cells reproducing rapidly and repeatedly by cell division. While the renewal of normal skin cell s takes approximately 311 hours, this process is elevated to take about 10 to 36 hours for psoriatic skin.

It is known that aromatic aldehydes and certain acetal derivatives thereof have a growth-inhibitory effect on human cells which is by its nature reversible. Growth inhibition induced by these compounds is primarily due to a reduction in the protein synthesis by cells. (Pettersen et al., Eur.J.Clin. Oncol. 19, 935–940 (1983) and Cancer Res. 45, 2085–2091 (1985)). The inhibition of protein synthesis is only effective as long as these agents are present in the cellular microenvironment. The synthesis of cellular protein is, for instance, rapidly restored to its normal level within one hour from the time when the agent is removed from the cells.

This leads to the effect that the normal cells are left without damage after treatment with the above compounds. Furthermore, the resulting inhibition of protein synthesis induces a prolonged cell cycle duration, such that a reduction of the cell production as well as a reduction of protein synthesis is achieved during treatment.

Examples of diseases which may be treated by the above compositions are rheumatoid arthritis, psoriatic arthritis, systemic lupus erythematosis (SLE), discoid lupus erythematosis (DLE), acne, Bechterew's arthritis, progressive systemic sclerosis (PSS) and seborrhea.

SUMMARY OF THE INVENTION

It has now been found that a class of aromatic aldehyde derivatives, e.g. arylidene diests and -alkoxyarylidene esters exert a surprisingly stronger protein synthesis inhibitory effect than the previously known and tested compounds.

DETAILED DESCRIPTION OF THE INVENTION

Figure 1:
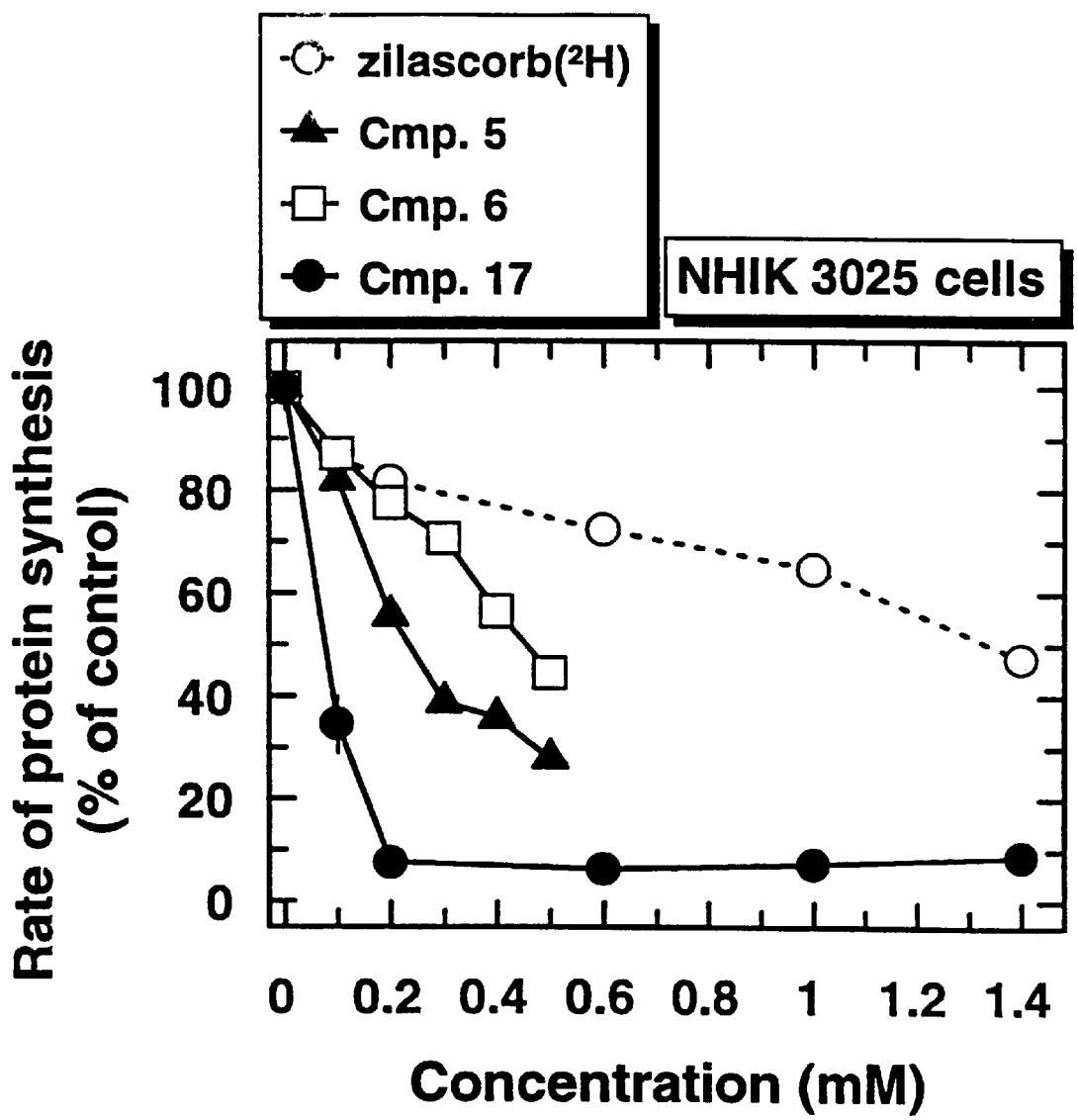
FIGS. 1–3 show the rate of protein synthesis in relationship to various compounds.

Thus the pharmaceutical compositions comprise compounds of the general formula (I) below:

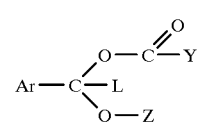

(I)

Formula I wherein L is H or D

Ar is phenyl or a 5- or 6-membered hetercyclic ring, the heteroatom being O, N or S.

The aromatic ring may be partly or fully deuterated, or further substituted, the substituents being the same or different, the said substituents may be alkyl which may be branched or linear with 1–20 carbon atoms, fluoroalkyl, alkenyl (branched or linear) with 2–20 carbon atoms, alkynyl (branched or linear) with 2–20 carbon atoms, phenyl, nitrophenyl, halogen, nitro, cyano, amino, monoalkylamino or dialkyylamino, wherein the alkyl groups may be the same or different and may have 1–20 carbon atoms, the said aromatic ring may further be substituted with, OR, wherein R may be D or alkyl with 1–20 carbon atoms, $CA(OR)_2$ wherein A may be H or D and R may be alkyl or acyl with 1–20 carbon atoms, COA wherein A may be H, D or alkyl of 1–20 carbon atoms, COOR wherein R may be H, D or alkyl of 1–20 carbon atoms, $CONR_1R_2$ wherein $R_1$ and $R_2$ may be the same or differnt and may be H, D or alkyl of 1–20 carbon atoms, when (I) is an acyclic acylal, i.e. Y and Z is not connected to form a ring, Ar cannot be an unsubstituted phenyl ring, Y in formula (I) may be H, D, or alkyl with 1–20 carbon atoms, alkenyl with 2–20 carbon atoms and with 1–6 double bonds, alkynyl with 2–20 carbon atoms and with 1–6 triple bonds and where the alkyl, alkenyl or alkynyl groups may be further substituted with alkyl, phenyl, nitrophenyl, halogen, nitro, cyano, amino, monoalkylamino or dialkylamino wherein the alkyl groups may be the same or different and may have 1–20 carbon atoms, Y in formula (I) may further be, OR wherein R may be H, D or alkyl with 1–20 carbon atoms, $CA(OR)_2$ wherein A may be H or D and R may be alkyl or acyl with 1–20 carbon atoms, COA wherein A may be H, D or alkyl of 1–20 carbon atoms, COOR wherein R may be H, D or alkyl of 1–20 carbon atoms, $CONR_1R_2$ wherein $R_1$ and $R_2$ may be the same or different and may be H, D or alkyl of 1–20 carbon atoms.

Z in formula (I) may be Y or COY, the substituents being the same or different.

The Z-O-C(Ar)L-O-CO-Y sequence in formula (I) may also form a 5- or 6-membered ring where Y and Z comprise a common alkyl chain of 1 or 2 carbon atoms which may be mono- or di- substituted (the substituents being the same or different, and situated on the same or different carbon atoms and may be alkyl with 1–20 carbon atoms, alkenyl with 2–20 carbon atoms and with 1–6 double bonds, alkynyl with 2–20 carbon atoms and with 1–6 triple bonds. The alkyl, alkenyl or alkynyl groups may be further substituted with alkyl, phenyl, nitophenyl, halogen, nitro, cyano, amino, monoalkylamino or dialkylamino wherein the alkyl groups may be the same or different and may have 1–20 carbon atoms, OR wherein R may be H, D or alkyl with 1–20 carbon atoms, $CA(OR)_2$ wherein A may be H or D and R may be alkyl or acyl with 1–20 carbon atoms, COA wherein A may be H, D or alkyl of 1–20 carbon atoms, COOR wherein R may be H, D or alkyl of 1–20 carbon atoms, $CONR_1R_2$ wherein $R_1$ and $R_2$ may be the same or different and may be H, D or alkyl of 1–20 carbon atoms.

The said Y-Z link may also comprise a fused aromatic ring and the aromatic ring may be substituted with alkyl, phenyl, nitrophenyl, halogen, nitro, cyano, amino, monoalkylamino or dialkylamino wherein the alkyl groups may be the same or different and may have 1–20 carbon atoms, OR wherein R may be H, D or alkyl with 1–20 carbon atoms, $CA(OR)_2$ wherein A may be H or D and R may be alkyl or acyl with 1–20 carbon atoms, COA wherein A may be H, D or alkyl of 1–20 carbon atoms, COOR wherein R may be H, D or alkyl of 1–20 carbon atoms, $CONR_1R_2$ wherein $R_1$ and $R_2$ may be the same or different and may be H, D or alkyl of 1–20 carbon atoms, and any pharmaceutical acceptable salt of formula I.

The preferred compounds which are present in the pharmaceutical compositions of this invention can be divided into some of the following subgroups represented by general formulas (II-III) below:

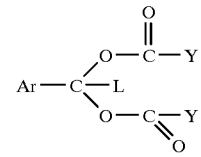

(II)

wherein all remaining substitutents have the above meanings;

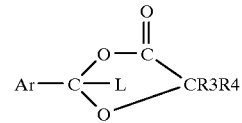

(III)

Further substituted with allyl, phenyl, nitrophenyl, halogen, nitro, cyano, amino, monoalkylamino or dialkylamino wherein the alkyl groups may be the same or different and may have 1–20 carbon atoms, OR wherein R may be H, D or allyl with 1–20 carbon atoms, $CA(OR)_2$ wherein A may be H or D and R may be alkyl or acyl with 1–20 carbon atoms, COA wherein A may be H, D or allyl of 1–20 carbon atoms, COOR wherein R may be H or alkyl of 1–20 carbon atoms, $CONR_1R_2$ wherein $R_1$ and $R_2$ may be the same or different and may be H, D or alkyl of 1–20 carbon atoms.

all remaining substitutents have the above meanings;

Especially preferred subgroups of compositions according to this invention are:

A. A pharmaceutical composition comprising a compound of formula (I) wherein Y is $CH_3$ and Z is $COCH_3$.

B. A pharmaceutical composition comprising a compound of formula (I) wherein Ar is mono- or disubstituted phenyl, the substituent or substituents which may be the same or different, are $CH_3$, $CF_3$, F, $NO_2$, CN, $CO_2$ $CH_3$, $CH(OCOCH_3)_2$, $CD(OCOCH_3)_2$.

C. A pharmaceutical composition comprising a compound of formula (I) wherein Ar is nitrofuranyl.

D. A pharmaceutical composition comprising a compound of formula (I) wherein Ar is phenyl.

E. A pharmaceutical composition comprising a compound of formula (I) wherein L is deuterium.

Especially preferred compositions are the following:

TABLE 1

| No. | Structural Formula | Name |
|---|---|---|
| 1 | | Benzylidene diacetate |
| 2 | | Benzylidene-$d_1$ diacetate |
| 3 | | 3-Methybenzylidene diacetate |
| 4 | | 4-Methybenzylidene diacetate |
| 5 | | 3-Nitrobenzylidene diacetate |
| 6 | | 4-Nitrobenzylidene diacetate |
| 7 | | 4-Cyanobenzylidene diacetate |

TABLE 1-continued

| No. | Structural Formula | Name |
|---|---|---|
| 8 | | 4-Fluorobenzylidene diacetate |
| 9 | | 4-Carbomethoxybenzylidene diacetate |
| 10 | | 4-Sodiumcarboxy benzylidene diacetate |
| 11 | | 3-Diacetoxymethylbenzylidene diacetate |
| 12 | | 3-Acetoxy-5-ethoxy-benzylidene diacetate |
| 13 | | Benzylidene-$d_1$ dibutanoate |
| 14 | | 4-Sodiumcarboxy benzylidene dibutanoate |

TABLE 1-continued

| No. | Structural Formula | Name |
|---|---|---|
| 15 | (structure) | Benzylidene dihexanoate |
| 16 | (structure) | 2-Furfurylidene diacetate |
| 17 | (structure) | 5-Nitro-2-furfurylidene diacetate |
| 18 | (structure) | Thiophene-2-carboxaldehyde diacetate |
| 19 | (structure) | Pyridine-3-carboxaldehyde diacetate |
| 20 | (structure) | 2-(R,S)-Phenyl-1,3-dioxolane-4-one |
| 21 | (structure) | (2R,S;5S)-2-Phenyl-5-methyl-1,3-dioxolane-4-one |
| 22 | (structure) | Benzylidene di-(α-chloroacetate) |

Preparation

The synthesis of benzylidene diacetate by the oxidation of toluene in the precence of acetic acid anhydride, has been known for a long time. Indeed, this route has been used for large-scale production of benzaldehyde, which, by formation and subsequent hydrolysis of the diacetate intermediate, is protected from over-oxidation. Benzylidene diacetate may of course also be syntesised by allowing acetic acid anhydride to act directly on benzaldehyde.

Also, the synthesis of aryl-substituted benzylidene diacetates from substituted benzaldehydes is well-known from the chemical litterature. The field is very well discribed in several standard organic textbooks. Klausener, A. et.al., Houben-Weyl, Methoden der Organischen Chemie, E14a/1, 711-, Thieme, Stuttgart 1991 gives an updated overview and many references are cited. The following references gives access to some key articles: Knoevenagel, E., Justus Liebigs Ann.Chem. 402 (1914), 111; Freeman, F. and Karachefski, E. M., J.Chem.Eng.Data 22 (1977), 355; Olah, G. A. and Mehrotra, A. K., Synthesis (1982), 962; Kochar, K. S., et.al. J.Org.Chem, 48 (1983), 1765; Cotelle, P. and Cotteau, J. P., Tetrahedron Lett. 33 (1992), 3855; Varma, R. S. et.al. Tetrahedron Lett., 34 (1993), 3207.

The use of different kinds of acidic catalyst is also drawing some attention. By the use of a resin-supported super acid in stead of conventional mineral acids, the method has been improved because aqeous work-up can be omitted (Olah, G. A. and Mehrotra, A. K., Synthesis (1982), 962).

By substituting the acetic acid anhydride with different carboxylic acid anhydrides, other benzylidene diesters may be formed similarily. The benzylidene diesters are generally called acvlals, in linguistic analogy to the structurally similar acetals. Benzylidene dibenzoate was synthesised already by Wegscheider, R. and Spat, E. (Monatsh.Chem. 30 (1909), 825). The synthesis of benzylidene dibutanoate is described by McKusick, B. C. (J.Am.Chem.Soc. 70 (1948), 1982) and by Man, E. H. et.al. (J.Am.Chem.Soc. 72 (1950), 847).

Also, some heterocyclic diacetates are known from the litterature. The diacetates from furfural or from thiophene-2-carboxaldehyde, and their 5-nitro counterparts, are referred to by the following authors: Herman, E. C. (U.S. Pat. No. 2,680,117, Jun. 1, 1954; Chem. Abstr. 1955, 49, 6313b); Patric, T. M. and Emerson, W. S. (J.Am.Chem.Soc. 74 (1952), 1356; Freeman, D. et.al., Aust.J.Chem. 29 (1976), 327 and Cymerman-Craig, J. and Willis, D. J.Chem.Soc. (1954), 1071.

The synthesis of acylals with two different ester moieties is also possible and, according to Klausener, A. et.al. (Houben-Weyl, Methoden der Organishen Chemie, E14a/1, 698, Thieme, Stuttgart 1991), the best way to achieve this goal is to go for a two step sequence. An arylidene-alpha-halo ester is prepared in the first step, and subsequentially, this intermediate is reacted with a carboxylic acid under basic conditions.

The condensation of aldehydes with di-carboxylic acids to give cyclic di-esters (acylals) and the condensation of hydroxy carboxylic acids to give cyclic alkoxy-esters (acylacetals) is also comprehensively described by Klausener, A. et.al. (Houben-Weyl, Methoden der Organischen Chemie, E14a/1, 716-, Thieme, Stuttgart 1991). However, whereas the cited references dealing with alifatic aldehydes are numerous, the corresponding benzylidene derivatives are sparsely described. The synthesis of some benzylidene dioxolanones and benzylidene dioxanones are never-the-less known from the litterture. Seebach, D. et.al., Tetrahedron 40 (1984), 1313; Farines, M. and Souliers, J.Bull.Soc.Chim.Fr. (1970), 332; and Mashraqui, S.H. et.al., J.Org.Chem. 49 (1984), 2513 gives examples of these kind of structures. The reaction is commonly carried out in a hydrocarbon medium, and the water formed during the condensation is preferably distilled off as an azeotropic mixture with the solvent.

Seebach and co-workers have pointed out an alternative route to some otherwise difficultly accessible dioxanones. The hydroxy carboxylic acid was first activated as the bis trimethylsilyl derivative, and then this intermediate was reacted with the aldehyde in the presence of trimethylsilyl triflate as a catalyst. (Seebach, D. et.al. Helv.Chim.Acta 70 (1987), 449).

What will be obvious from the above description is that several substances comprised in the present patent application are known from the existing chemical literature and can readily be prepared by a person skilled in the art. Indeed, many acylals, especially of the benzylidene diacetate type, have already been synthesised. However, none of these substances, to our knowledge, have ever been proposed as therapeutic agents for treatment of any diseases originating from elevated cell proliferation, especially cancer.

The acyclic derivatives according to the precent invention may thus be prepared by reacting the corresponding aromatic- or heterocyclic aldehyde with a carboxylic acid anhydride in the precence of an acidic catalyst. The catalyst may be a mineral acid, ex. sulfuric acid, an organic acid, ex. p-toluene sulfonic acid or a resin supported super acid, ex. Nafion NR 50.

The cyclic derivatives of the precent invention may be prepared by condensation of the corresponding aldehyde with a hydroxy-carboxylic acid or a trimethylsilyl-activated hydroxy-carboxylic acid in the precence of an appropriate catalyst.

The reaction may conveniently be carried out in an inert solvent such as carbon tetrachloride, dichloromethane, pentane, toluene or the like, or alternatively in an excess of anhydride without any additional solvent.

The specific reaction conditions, solvent and catalyst used will in each individual case depend on the solubility and reactivity of the reactants and of the property of the product.

The compounds of formula 1 wherein L is deuterium may be prepared as described above, but starting with aromatic- or heterocyclic aldehydes which are deuterated in the formyl position.

The following examples are illustrative of how the compounds of the present invention may be prepared.

EXAMPLE 1

Benzylidene Diacetate

To an ice/water cooled solution of benzaldehyde (5.0 g, 0.047 mol) in an excess of acetic acid anhydride (50 ml), was added conc. sulfuric acid (5 dr.). After ½ hr., the water bath was removed, and the reaction mixture was stirred at room temperature for additional 2 hr. The excess anhydride was then evaporated and the colourless oily residue was distilled (140–145° C./15 mmHg). The distillate solidified upon standing, m.p. 45–47.5° C. Yield: 5.2 g, 53% of the theoretical. NMR (CDCl$_3$), d (ppm) rel. to TMS: 7.68 (s, 1H, CH(OAc)$_2$); 7.52 and 7.42 (m, 2+3H, Ar-H) and 2.15 (s, 6H, CH$_3$).

EXAMPLE 2

Benzylldene-d$_1$ Diacetate

Benzaldehyde-d$_1$ (10.0 g, 0.093 mol) and acetic acid anhydride (9.5 g, 0.093 mol) were dissolved in carbontetrachloride (10 ml) at 0° C. Nafion NR 50 (280 mg) was added and the reaction mixture stirred for ½ hr. The ice/water bath was removed and the reaction continued at room temperature. After 5 hr. an additional amount of 0.95 g anhydride and 300 mg catalyst were added. The reaction was disrupted after 24 hr. by filtering off the catalyst (washing with ether) and evaporating the filtrate. The residue was distilled (b.p. 135–136° C./15 mmHg), giving a white solid, m.p. 44.5–47.5° C. The yield was 13.9 g, 71% of the theoretical. $^1$H- and $^{13}$C NMR (CDCl$_3$), d (ppm) rel. to TMS: 7.53 and 7.43 (m, 2+3H, Ar-H) and 2.14 (s, 6H, CH$_3$); 168.743 (C=O), 135.337, 129.726, 128.561 and 126.627 (Ar), ca. 89 (CD(OAc)$_2$)) and 20.826 (CH$_3$).

EXAMPLE 3

3-Methylbenzylidene Diacetate

3-Methylbenzaldehyde (4.57 g, 0.038 mol) was dissolved in an excess of acetic acid anhydride (10 ml) and 4 drops conc. sulfuric acid added under stirring. The resulting mixture was allowed to react at room temperature for 1.5 hr. Hexane (30 ml) was then added and the resulting two phases washed twice with 10% aqueous NaHCO$_3$ (20 ml). The organic phases was dried (MgSO$_4$) and evaporated. The crude product was distilled under reduced pressure (78° C./0.12 mbar) to give a colourless oil. The yield was 3.6 g, 43% of the theoretical. $^1$H- and $^{13}$C NMR (CDCl$_3$), d (ppm) rel. to TMS: 7.66 (s, 1H, CH(OAc)$_2$), 7.36–7.20 (m, 5H, Ar-H), 2.38 (s, 3H, Ar-CH$_3$) and 2.12 (s, 6H, COCH$_3$); 168.695 (C=O), 138.304, 135.288, 130.434, 128.443, 127.180 and 123.621 (Ar), 89.690 (CH(OAc)$_2$), 21.270 (Ar-CH$_3$) and 20.778 (COCH$_3$).

EXAMPLE 4

4-Methylbenzylidene Diacetate

4-Methylbenzaldehyde (4.01 g, 0.033 mol) was dissolved in an excess of acetic acid anhydride (10 ml) and 5 drops conc. sulfuric acid added under stirring. The resulting mixture was allowed to react at room temperature for 1½ hr. and excess anhydride removed by evaporation. The residue was washed with 70% ethanol (20 ml), before dissolving in acetone and filtering through a bed of silica gel. Evaporating of the solvent gave white crystals, 2.56 g, 35% of the theoretical. $^1$H- and $^{13}$C NMR (CDCl$_3$), d (ppm) rel. to TMS: 7.66 (s, 1H, CH(OAc)$_2$), 7.43 and 7.23 (q, 2+2H, Ar-H), 2.38 (s, 3H, Ar-CH$_3$) and 2.12 (s, 6H, COCH$_3$); 168.703 (C=O), 139.693, 132.519, 129.165 and 126.519 (Ar), 89.684 (CH(OAc)$_2$), 21.194 (Ar-CH$_3$) and 20.775 (COCH$_3$).

EXAMPLE 5

3-Nitrobenzylidene Diacetate

3-Nitrobenzaldehyde (20.0 g, 0.132 mol) and acetic acid anhydride were dissolved in carbontetrachloride (50 ml). Nafion NR 50 (600 mg) was added and the reaction mixture stirred under N$_2$-atmosphere at 35° C. overnight. An additional amount of 3.0 g anhydride was added and the reaction mixture left over night again. The catalyst was filtered off and the filtrate evaporated. The residue was a yellow oil together with some precipitated crystals, which were filtered off (washing with cold hexane). The filtrate was evaporated again and the residue recrystallized from hexane (900 ml). The product formed slightly yellow crystals, m.p. 67–70° C. The yield was 21.1 g, 63 % of the theoretical. $^1$H- and $^{13}$C NMR (CDCl$_3$), d (ppm) rel. to TMS: 8.45–7.61 (m, 3×1H, Ar-H), 7.79 (s, 1H, Ar-CH(OAc)$_2$) and 2.19 (s, 6H, CH$_3$); 168.583 (C=O), 148.344, 137.496, 132.956, 129.742, 124.578, 121.881 (Ar), 88.337 (CH(OAc)$_2$) and 20.758 (CH$_3$).

EXAMPLE 6

4-Nitrobenzylidene Diacetate

4-Nitrobenzaldehyde (10.0 g, 0.066mol) and acetic acid anhydride (7.4 g, 0.073 mol) were mixed in carbontetrachloride (25 ml). Nafion NR 50 (300 mg) was added and the reaction mixture stirred under $N_2$-atmosphere at 35° C. for several days. The catalyst was filtered off (washing with carbontetrachloride) and the filtrate concentrated until a slightly yellow precipitate was formed. The crystals were filtered off, washed with ether and used without further purification. M.p.: 124–126° C. The yield was 4.6 g, 27% of the theoretical. $^1$H- and $^{13}$C NMR (CDCl$_3$), d (ppm) rel. to TMS: 8.27 and 7.71 (q, 2+2H, Ar-H), 7.74 ppm (s, 1H, CH(OAc)$_2$) and 2.19 (s, 6H, CH$_3$); 168.464 (C=O), 148.466, 141.819, 127.754 and 123.696 (Ar), 88.171 (CH(OAc)2) and 20.599 (CH$_3$).

EXAMPLE 7

4-Cyanobenzylidene Diacetate

4-Cyanobenzaldehyde (10.0 g, 0.076 mol) and acetic acid anhydride (7.8 g, 0.076 mol) were dissolved in carbontetrachloride (15 ml). Nafion NR 50 (300 mg) was added and the reaction mixture stirred under $N_2$-atmosphere at room temperature. After 5 hr. an additional amount of 4.0 g anhydride was added, and the reaction mixture was left for several days. The catalyst was filtered off, and the filtrate evaporated. The residue was taken up in chloroform (230 ml) and unreacted starting material precipitated by adding hexane (100 ml) and then filtered off. The filtrate was evaporated and the dissolution/precipitation sequence repeted. The crude product was finally recrystallized from ether giving white crystals, m.p.: 104–107° C. The yield was 5.9 g, 34% of the theoretical. $^1$H- and $^{13}$C NMR (CDCl$_3$), d (ppm) rel. to TMS: 7.72 and 7.63 (q, 2+2H, Ar-H), 7.69 (s, 1H, CH(OAc)$_2$) and 2.17 (s, 6H, CH$_3$); 168.554 (C=O), 140.103, 132.442, 127.512, 118.166, 113.616 (Ar and C=N), 88.513 (CH(OAc)$_2$) and 20.737 (CH$_3$).

EXAMPLE 8

4-Fluorobenzylidene Diacetate

4-Fluorobenzaldehyde (10.0 g, 0.081 mol) and acetic acid anhydride (8.23 g, 0.081 mol) were dissolved in carbontetrachloride (10 ml). Nafion NR 50 (300 mg) was added and the reaction mixture stirred in $N_2$-atmosphere at room temperature for 21 hr. The catalyst was filtered off and the filtrate evaporated, giving a colourless oil which solidified upon standing. This crude product was distilled through a short path (hot water condenser), b.p.: 68.5–71.5° C./0.1 mbar.

The product was a white solid, m.p.: 52–53.5° C. The yield was 14.9 g, 82% of the theoretical. $^1$NMR (CDCl$_3$) d (ppm) rel. to TMS: 7.67 (s, 1H, CH(OAc)$_2$), 7.52 and 7.11 (q, 2+2H, Ar-H) and 2.11 (s, 6H, CH$_3$).

EXAMPLE 9

4-Carbomethoxybenzylidene Diacetate

To an ice/water cooled mixture of methyl-4-formyl benzoate (10.0 g, 0.061 mol) and acetic acid anhydride (50 ml) was added conc. sulfuric acid (5 dr.). When the reaction mixture had reached 0° C. again, the water bath was removed. After 2 hr., the reaction mixture was evaporated and the residue crystallized from hexane. The first crop formed fluffy, white crystals of acceptable purity. The second crop was purified further on a Lobar C silica column, eluting first with ethylacetate/hexan 1:10, then with 1:1. (M.p. 64–67° C.). The total yield (crystallization and chromatography) was 4.85 g, 30% of the theoretical. $^1$H NMR (CDCl$_3$) d (ppm) rel. to TMS: 8.09 and 7.60 (q, 2+2H, Ar-H), 7.72 (s, 1H, CH(OAc)$_2$) and 2.14 (s, 1H, CH$_3$).

EXAMPLE 10

4-Sodiumcarboxybenzylidene Diacetate

4-Carboxybenzaldehyde (10.0 g, 0.067 mol) and acetic acid anhydride (35 ml) were mixed under $N_2$-atmosphere. Nafion NR 50 (300 mg) was added and the reaction mixture stirred at room temperature for two days. The catalyst was filtered off and the reaction mixture was also filtered, washing with ether.. The filtrate was evaporated and stirred with a 5% NaHCO$_3$-solution (100 ml). A solid lump which did not dissolve was taken out. The water phase was freeze-dried and purified on a Lobar C RP-8 reversed phase column, eluting with 10% methanol in water. The product from several runs were freeze-dried and combined, giving a pure white, fluffy powder (1.0 g). $^1$H NMR (D$_2$O), d (ppm) rel. to TMSP: 7.93 and 7.63 (q, 2+2H, Ar-H), 7.68 (s, 1H, CH(OAc)$_2$) and 2.19 (s, 6H, CH$_3$).

EXAMPLE 11

3-Diacetoxymethylbenzylidene Diacetate

Isophtalaldehyde (10.0 g, 0.075 mol) and acetic acid anhydride (16.7 g, 0.164 mol) were mixed under $N_2$-atmosphere in carbontetrachloride (25 ml). Nafion NR 50 was added and the reaction mixture stirred at 30° C. for several days. During this period additional amounts of catalyst (100 mg) and solvent (5 ml) were added. The catalyst was filtered off and also the reaction mixture was filtered, washing with ether. The crude solid was recrystallized from cyclohexane (540 ml), giving white crystals, m.p. 110–130° C. The yield was 10.3 g, 41% of the theoretical. $^1$H- and $^{13}$C NMR (CDCl$_3$), d (ppm) rel. to TMS: 7.72 (s, 1H, CH(OAc)$_2$), 7.70–7.42 (m, 1+2+1H, Ar-H) and 2.13 (s, 6H, CH$_3$); 168.591 (C=O), 135.908, 128.885, 128.047 and 124.879 (Ar), 89.072 (CH(OAc)$_2$) and 20.717 (CH$_3$).

EXAMPLE 12

3-Acetoxy-5-ethoxy-benzylidene Diacetate

3-Ethoxy-4-hydroxybenzaldehyde (4.26 g, 0.025 mol) was mixed with an excess of acetic acid anhydride (10 ml). By adding conc. sulfuric acid (3 dr.), the colour changed from orange to dark red. The resulting solution was stirred at room temperature for 3 hr. The reaction mixture was then dissolved in CH$_2$Cl$_2$ before washing with aqueous NaHCO$_3$. The organic phase was dried (MgSO$_4$) and evaporated. The crude product was repeatedly recrystallized from CHCl$_3$, and finally the white crystalline solid was precipitated from CHCl$_3$ by the addition of pentane. NMR spectroscopy indicated that the product was 3-acetoxy-5-ethoxy-benzylidene-diacetate, which is concidered to be formed by acetylation and an unexpected rearrangement of the 4-hydroxy-group of the aldehyde. $^1$H- and $^{13}$C NMR (CDCl$_3$), d (ppm) rel. to TMS: 7.61and 7.25 (s+s, 1+1H, Ar-H), 7.12 (s, 2H, Ar-H+CH(OAc)$_2$), 4.11 (q, 2H, CH$_3$CH$_2$O), 2.25 (s, 3H, Ar-OCOCH$_3$), 2.10 (s, 6H, CH(OCOCH$_3$)$_2$) and 1.35 (t, 3H, OCH$_2$CH$_3$); 169.230 (CH(OCOCH$_3$)2), 168.870 (Ar-OCOCH$_3$), 151.619,142.068, 135.418, 123.697, 119.540 and 112.749 (Ar), 89.838 (CH(OAc)$_2$), 65.075 OCH$_2$), 20.669 (CH(OCOCH$_3$)$_2$), 20.389 (Ar-OCOCH$_3$) and 14.888 (OCH$_2$CH$_3$).

EXAMPLE 13

Benzylldene-d$_1$ Dibutanoate

Benzaldehyde-d$_1$ (10.0 g, 0.093 mol) and butyric acid anhydride (15.0 g, 0.095 mol) were dissolved in carbontetrachloride under N$_2$-atmosphere. Nafion NR 50 was added and the reaction mixture stirred at room temperature for 3 days. The catalyst was filtered off, and the filtrate evaporated. The residue was distilled giving a colourless oil, b.p. 157–163° C./5 mbar. The yield was 17.7 g, 75% of the theoretical. $^1$H NMR (CDCl$_3$), d (ppm) rel. to TMS: 7.53 and 7.42 (m, 2+3H, Ar-H), 2.38 (double t, 4H, COCH$_2$), 1.69 (m, 4H, CH$_2$CH$_2$CH$_3$) and 0.97 (t, 6H, CH$_3$).

EXAMPLE 14

4-Sodiumcarboxybenzylidene Dibutanoate

4-Carboxybenzaldehyde (8.6 g, 0.057 mol) and butyric acid anhydride (45 ml) were mixed under N$_2$-atmosphere. Nafion NR 50 (300 mg) was added and the reaction mixture stirred at 30° C. for several days. During this period an additional amount of catalyst (150 mg) was added. The catalyst was filtered off, and also the reaction mixture was filtered (washing with hexane). The filtrate was evaporated and the residue mixed with 5% NaHCO$_3$-solution (200 ml). An undissolved fraction was removed by decanting off the solution. The water phase was freeze-dried and purified on a Lobar C RP-8 reversed phase column, eluting with methanol/water 1:1. The product from several runs were freeze-dried and combined, giving a white powder (3.1 g). $^1$H NMR (D$_2$O) d (ppm) rel. to TMSP: 7.95 and 7.63 (q, 2+2H, Ar-H), 7.73 (s, 1H, CH(OCOC$_3$H$_7$)$_2$), 2.43 (t, 4H, COCH$_2$), 1.62 (m, 4H, CH$_2$CH$_2$CH$_3$) and 0.90 (t, 6H, CH$_3$). $^{13}$C NMR (D$_2$O/dioxan) d (ppm) rel. to TMSP: 174.117 (CO$_2$Na), 173.434 (COC$_3$H$_7$), 137.970, 137.048, 129.352 and 126.146 (Ar), 88.499 (CH(OCOC$_3$H$_7$)$_2$), 35.476 (COCH$_2$), 17.810 (CH$_2$CH$_2$CH$_3$) and 12.779 (CH$_3$).

EXAMPLE 15

Benzylidene Dihexanoate

Benzaldehyde (26.3 g, 0.25 mol) and hexanoic acid anhydride (53.3 g, 0.25 mol) were dissolved in carbontetrachloride (200 ml) under N$_2$-atrnosphere. Catalytic amounts of sulfuric acid was added and the reaction mixture stirred at room temperature for 1 hr. The reaction mixture was evaporated over night, the residue dissolved in hexane and the solution filtered through a bed of silica. The filtrate was purified on a silica column, eluting with hexane. The evaporated eluate was a colourless oil and the yield was 14.0 g, 18% of the theoretical. $^1$H- and $^{13}$C NMR (CDCl$_3$) d (ppm) rel. to TMS: 7.72 (s, 1H, CH(OC$_5$H$_{11}$)2), 7.58–7.39 (m, 5H, Ar-H), 2.37 (double t, 4 H, COCH$_2$), 1.64 (m, 4H, COCH$_2$CH$_2$), 1.30 (m, 4H,CH$_2$CH$_2$CH$_3$) and 0.88 (t, 6H, CH$_3$); 171.524 (C=O), 135.688, 129.523, 128.466 and 126.547 (Ar), 89.398 (CH(OC$_5$H$_{11}$)$_2$), 33.965, 31.030, 24.235 and 22.179 (CH$_2$) and 13.777 (CH$_3$).

EXAMPLE 16

2-Furfurylidene Diacetate

Furan-2-carboxaldehyde (4.85 g, 0.050 mol) was dissolved in an excess of acetic acid anhydride (10 ml). By the addition of 2 drops conc. sulfuric acid, the solution turned black. The resulting mixture was stirred at room temperature for 5 hr. The mixture was then diluted with CHCl$_3$ before washing with aqueous NaHCO$_3$. The organic phase was dried (MgSO$_4$) and evaporated. The black crude product was dissolved in diethyl ether and treated with activated charcoal. The liquid was evaporated, and the residue dissolved in hexane. Unsoluble impurities were removed, and the hexane was evaporated to give white or weakly pink crystals. The yield was 2.12 g, 21% of the theoretical. $^1$H- and $^{13}$C NMR (CDCl$_3$), d (ppm) rel. to TMS: 7.73 (s, 1H, CH(OAc)2), 7.48, 6.55 and 6.41 (m, 3×1H, Ar-H), 2.14 (s, 6H, CH$_3$); 168.308 (C=O), 147.751, 143.562, 110.276 and 109.639 (Ar), 83.328 (CH(OAc)$_2$) and 20.564 (CH$_3$).

EXAMPLE 17

5-Nitro-2-furfurylidene Diacetate

This substance was a commercial sample from FLUKA and was used without further purification. The identity was confirmed by NMR analysis.

EXAMPLE 18

Thiophene-2-carboxaldehyde Diacetate

Thiophene-2-carboxaldehyde (5.66 g, 0.050 mol) was dissolved in an excess of acetic acid anhydride (10 ml) and 3 drops conc. sulfuric acid added under stirring. The resulting green mixture was allowed to react at room temperature for 2.5 hr. The reaction mixture was then diluted with CHCl$_3$ (25 ml) before washing twice with 10% aqueous NaHCO$_3$ (20 ml). The organic phase was dried (MgSO$_4$) and evaporated. The crude product was dissolved in hexane, and insoluble impurities were removed. The hexane solution was then treated with activated charcoal, to give a colourless liquid. Evaporation of the solvent gave white or weakly pink crystals. The yield was 3.8 g, 35% of the theoretical. 1H- and 13C NMR (CDCl3), d (ppm) rel. to TMS: 7.93 (s, 1H, CH(OAc)$_2$) 7.49, 7.27 and 7.02 (m, 3×1H, Ar-H) and 2.12 (s, 6H, CH$_3$); 168.386, 137.867, 127.179,126.917 and 126.599 (Ar), 86.227 (CH(OAc)$_2$) and 20.663 (CH$_3$).

EXAMPLE 19

Pyridine-3-carboxaldehyde Diacetate

Pyridine-3-carboxaldehyde (5.45 g, 0.051 mol) was dissolved in an excess of acetic acid anhydride (10 ml) and 4 drops conc. sulfuric acid added under stirring. The resulting red mixture was allowed to react at 70–75° C. for 7 days. The cooled, black coloured reaction mixture was diluted with CHCl$_3$, washed twice with 10% aqueous NaHCO$_3$ and then several times with brine. The organic phase was dried (MgSO$_4$) and evaporated. The black crude product was dissolved in CHCl$_3$, and impurities precipitated as pentane was added. Precipitates were removed. The solution was evaporated and the residual product distilled (Kugelrohr) under reduced pressure (140° C./0.2 mbar) to give a colourless oil. $^1$H- and $^{13}$C NMR (CDCL$_3$), d (ppm) rel. to TMS: 8.80, 8.68, 7.83 and 7.37 (m, 4×1H, Ar-H), 7.73 (s, 1H, CH(OAc)$_2$) and 2.14 (s, 6H, CH$_3$); 168.443 (C=O), 150.778, 148.154, 134.303, 131.172 and 123.253 (Ar), 87.988 (CH(OAc)$_2$) and 20.587 (CH$_3$).

EXAMPLE 20

(2R,S)-Phenyl-1,3-dioxolane-4-one

To a suspension of glycolic acid (7.6 g, 0.100 mol) in dichloromethane (200 ml), triethylamine (31.2 g, 0.22 mol)

was added at 0–5° C. At the same temperature, trimethyl chlorosilane (28.8 ml, 0.22 mol) was added. This white suspension was stirred for 20 hr., filtered and evaporated to remove $CH_2Cl_2$. Pentane (150 ml) was added to the residue to precipitate $Et_3NHCl$. The suspension was filtered through a 5 μm Millipore filter and evaporated. Fractionated destillation of the crude product under reduced pressure (28° C./1.0 mbar) gave a colourless liquid of acceptable purity. The yield was 15.7 g, 71% of the theoretical. The identity of the thus formed bis-(trimethylsilyl)-glycolic acid was confirmed by NMR spectroscopy.

Catalytic amounts of trimethylsilyl trifluoromethanesulphonate (0.4 ml) was added to a solution containing bis-(trimethylsilyl)-glycolic acid (8.0 g, 36 mmol) and benzaldehyde (2.6 g, 24 mmol) in dichloromethane (70 ml) at −75° C. The solution was stirred at this temperature for 20 hr. Pyridine (0.2 g, 2.5 mmol) was added and the temperature allowed to increase to room temperature. After cromatographic separation (silica/$CH_2Cl_2$), the remaining impurities were removed by evaporation under reduced pressure (0.5 torr) at 20° C. for 16 hr. The yield was 2.5 g, 42% of the theoretical. $^1H$- and $^{13}C$ NMR ($CDCl_3$), d (ppm) rel. to TMS: 7.55–7.41 (m, 5H, Ar-H), 6.51 (s, 1H, Ar-CH) and 4.45 (q, 2H, $CH_2$); 171.122 (C=O), 134.521, 130.495, 128.669 and 126.328 (Ar), 105.155 (Ar-CH) and 64.137 ($CH_2$).

EXAMPLE 21

(2R,S;5S)-2-Phenyl-5-methyl-1,3-dioxolane-4-one

Benzaldehyde (88.5 g, 0.834 mol) and L(+)-lactic acid were mixed in toluene (600 ml) in a 1 L three-necked flask equipped with a Dean-Stark water trap. Catalytic amounts of p-toluene sulfonic acid was added and the reaction mixture refluxed with stirring over night. The reaction mixture was cooled and washed with 10% $NaHCO_3$-solution (600 ml) in a separating funnel. The organic phase was dried ($MgSO_4$), filtered and evaporated. The crude product was dissolved in ether, and pentane was added until the solution became cloudy. By cooling in an acetone/dry ice bath, a slightly yellow precipitate was formed. This was isolated (m.p. 50–53° C.) and shown to be a 4:1 cis/trans isomeric mixture of the title compound. The yield was 12.4 g, 42% of the theoretical. $^1H$- and $^{13}C$ NMR (acetone-$d_6$), d (ppm) rel. to TMS: 7.65–7.46 (m, 5H, Ar-H), 6.71 and 6.51 (s+s, 1H, Ar-CH), 4.69 (q, 1H, OCHCH$_3$) and 1.52 (d, 3H, $CH_3$); 174.167 (C=O)136.248, 131.322, 130.984, 129.473, 127.836 and 127.293 (Ar), 103.585 (Ar-CH), 72.519 (OCHCH$_3$) and 16.544 and 15.983 ($CH_3$).

EXAMPLE 22

Benzylidene di-(alpha-chloroacetate)

Benzaldehyde (10.0 g, 0.094 mol) and chloroacetic acid anhydride (16.1 g, 0.094 mol) were dissolved in carbontetrachloride (50 ml) under $N_2$ atmosphere. Nafion NR 50 (240 mg) was added and the reaction mixture stirred at 35° C. over night. An additional amount of benzaldehyde (5.0 g) and catalyst (120 mg) was added and the reaction continued for several days. The catalyst was filtered off and the filtrate evaporated. The residue was distilled under reduced pressure (B.p. 123–125° C./0.1 mbar) giving a slightly yellow oil, which solidified upon standing. The yield was 7.9 g, 30% of the theoretical. $^1H$ NMR ($CDCl_3$), d (ppm) rel. to TMS: 7.75 (s, 1H, CH(OCO—)$_2$), 7.57–7.41 (m, 2+3H, Ar-H) and 4.14 (d, 4H $CH_2Cl$).

Biological Experiments

In the following in vitro experiments, the rate of protein synthesis was measured for a compound from the prior art, which is deuterated sodium 5,6-O-benzylidene-$d_1$-L-ascorbic acid (zilascorb($^2$H)), and for 14 compounds according to the present invention.

Cell Culturing Techniques

Human cells of the established line NHIK 3025, originating from a cervical carcinoma in situ (Nordbye, K. and Oftebro, R., Exp. Cell Res., 58: 458, 1969; Oftebro, R. and Nordbye, K., Exp. Cell Res., 58: 459–460, 1969) were cultivated in medium E2a (Puck et al., J. Exp. Med., 106: 145–165, 1957) supplemented with 20% human (prepared at the laboratory) and 10% horse serum (GIBCO).

The A549 human lung carcinoma cell line (ATCC CCL 185) was purchased from the American Type Culture Collection. The cells were cultivated in Dulbecco's modification of Eagles Minimum Essential Medium (D-MEM) supplemented with 10% heat-inactivated foetal calf serum (GIBCO).

V79 379-A cells (Ford and Yerganian, J. Natl. Cancer Inst., 21: 393–425, 1958) were provided by Dr. Revesz, Karolinska Institute, Stockholm, Sweden in 1976. These cells were cultivated in Eagles Minimum Essential Medium (MEM) supplemented with 10% newborn calf serum.

T-47D human mammary carcinoma cells (Keydar et al., Europ. J. Cancer, 15: 659–670, 1979) were cultivated in RPMI 1640 medium supplemented with 10% foetal calf serum.

All cells were routinely grown as monolayers in tissue culture flasks. The cells were kept in continuous exponential growth by frequent reculturing, i.e. every second or third day. During reculturing, as well as during experiments, the cells were kept in incubators (stand-alone or walk-in) at 37° C.

Spheroid growth was initiated by trypsinising a stock culture, removing trypsin solution by centrifugation (250× g), and seeding approximately 100,000 cells in a 25 cm² plastic tissue culture flask (NUNC, Denmark) containing 12 ml of medium (Wibe et al., Cell Tissue Kinet., 14: 639–651, 1981). This flask was then rocked (30 periods per minute) for 24 hours on a tilting platform (Rotary Mixer, Labinco, The Netherlands) in a 37° C. room. The constant motion prevented attachment of the cells to the bottom of the flask, and the cells formed aggregates each of which consisted of from 10 to 100 cells. After the 24 hour agitation, the aggregates were transferred to a 75 cm² plastic tissue culture flask previously coated with a thin (1 ml per 25 cm²) layer of 1% sterilised agar (Bactoagar, Difco, U.S.A.). The agar coating prevented attachment of the aggregates to the bottom of the flask. The medium (50 ml per flask) was changed three times per week during the growth period. After one week of growth, 200 spheroids of similar size were sorted out per flask using a Pasteur pipette. Spheroid volume growth was measured by transferring individual spheroids into agar-coated (0.15 ml) wells (diameter 16 mm) on plastic tissue culture multidishes (Falcon, Oxnard, U.S.A.), one spheroid per well. The medium was changed daily. Two perpendicular diameters on the spheroids were measured using a calibrated ocular micrometer in an inverted phase contrast microscope. The average volume was calculated as the mean of 48 spheroids using the formula (p/6)×diameter³. All volumes have been normalised such that the volume immediately after treatment was set to 1.

Anticancer effects were tested in vivo by daily oral administration via gastric intubation of a test compound solution. Female athymic mice (BALB/C/nu/nu/BOM were used. Tumors of either A549 human lung carcinoma or SK-OV human ovarian carcinoma were implanted subcutaneously onto the hind flank of each mouse at the age of 9 weeks when the mean animal weight was 25.5±0.3 g. Drug administration began approximately 4 weeks later when the tumor diameters were 3 to 6 mm. Drugs were dissolved in 0.9%. saline.

Protein Synthesis

The rate of protein synthesis was calculated as described previously (Rønning et al., J. Cell Physiol., 107: 47–57, 1981). Briefly, cellular protein was labelled to saturation during a 2–4 day preincubation with [$^{14}$C]valine of constant specific radioactivity (0.5 Ci/mol) prior to the experiment. This was achieved by using a high concentration of valine so that the dilution of [$^{14}$C]valine by intracellular valine and by proteolytically generated valine will be negligible (Rønning et al., Exp. Cell Res., 123: 63–72, 1979), thus keeping the specific radioactivity at a constant level. The rate of protein synthesis was calculated from the incorporation of [$^{3}$H] valine of constant specific activity. The incorporated [$^{3}$H] measurements were related to the total of [$^{14}$C] radioactivity in protein at the beginning of the respective measurement periods and expressed as the percentage per hour.

Results The protein synthesis inhibition induced by zilascorb($^{2}$H) and 14 compounds of the present invention was assayed in several mammalian cell lines. Several concentrations were assayed for each compound, with 3-4 replicate samples per concentration.

In FIG. 1 the rate of protein synthesis (as % of control rate) is shown in relation to the concentration of two nitrobenzylidene diacetates (Compounds 5 and 6) and one nitrofiran (Compound 17) in human NHIK 3025 cervix carcinoma cells. The treatment period was for 1 hour during which the cell culture medium contained [$^{3}$H]valine in addition to the test compound. As compared to the effect of the prior art compound zilascorb($^{2}$H), the protein synthesis was inhibited to a far greater degree by all three compounds with the nitrofuran Compound 17 inducing the strongest inhibition of protein synthesis.

Figure 2:
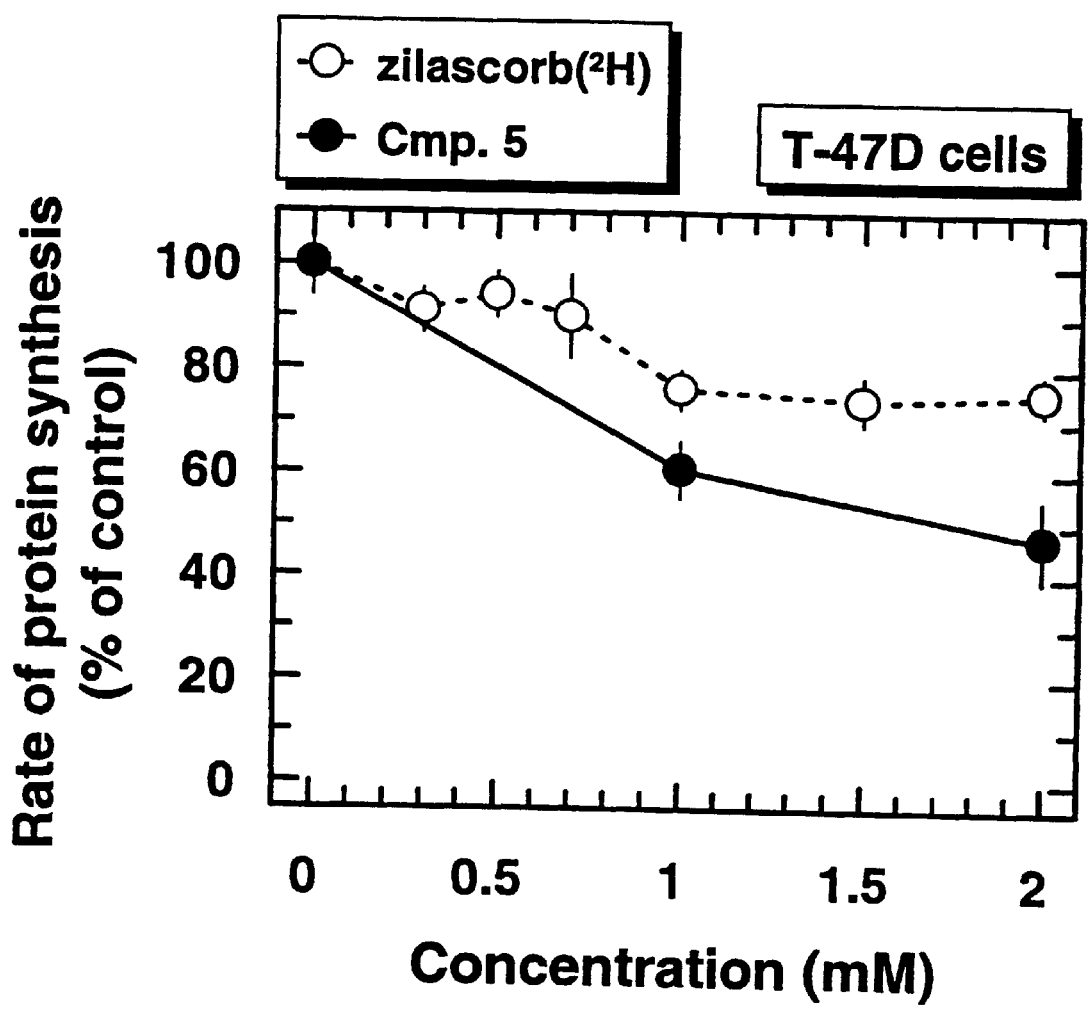

In FIG. 2, the rate of protein synthesis (as % of control rate) is shown in relation to the concentration of the nitrobenzylidene diacetate Compound 5 used in the treatment of human T-47D mammary carcinoma cells cultivated in vitro. Treatment conditions were as described in FIG. 1. The nitrobenzylidene diacetate Compound 5 induced a stronger inhibition of protein synthesis than the prior art compound zilascorb($^{2}$H).

Figure 3A:
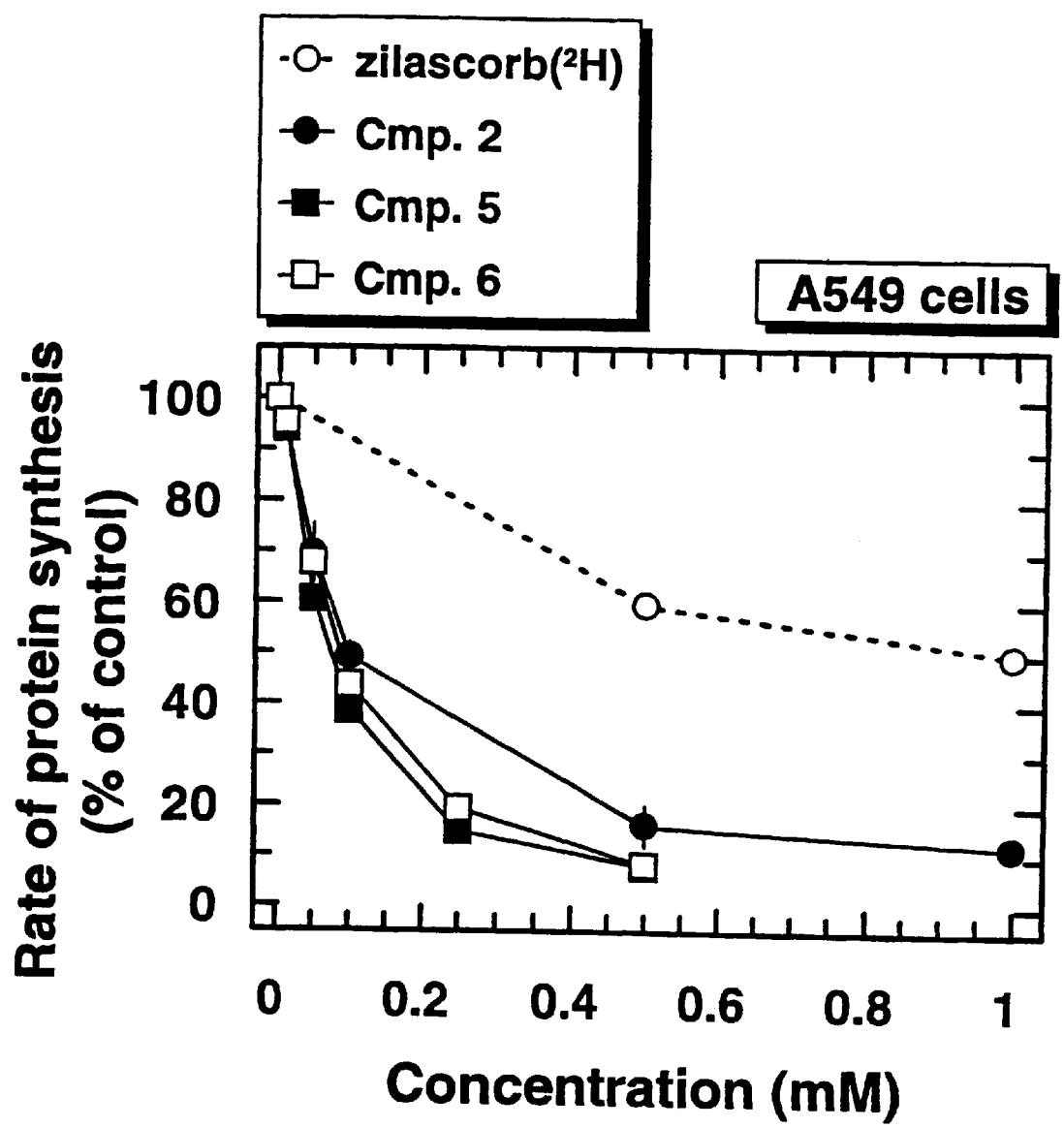
Figure 3B:
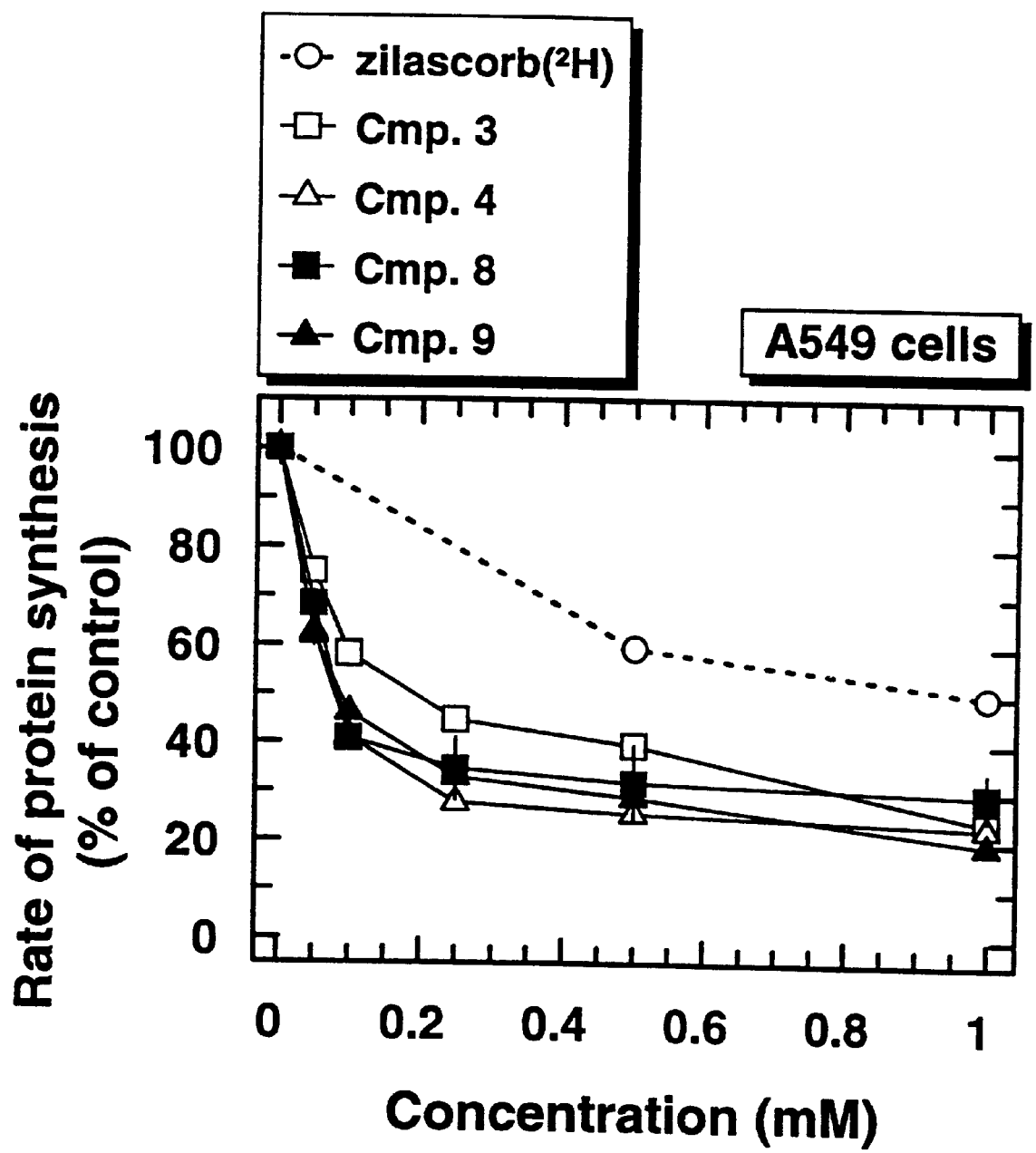
Figure 3C:
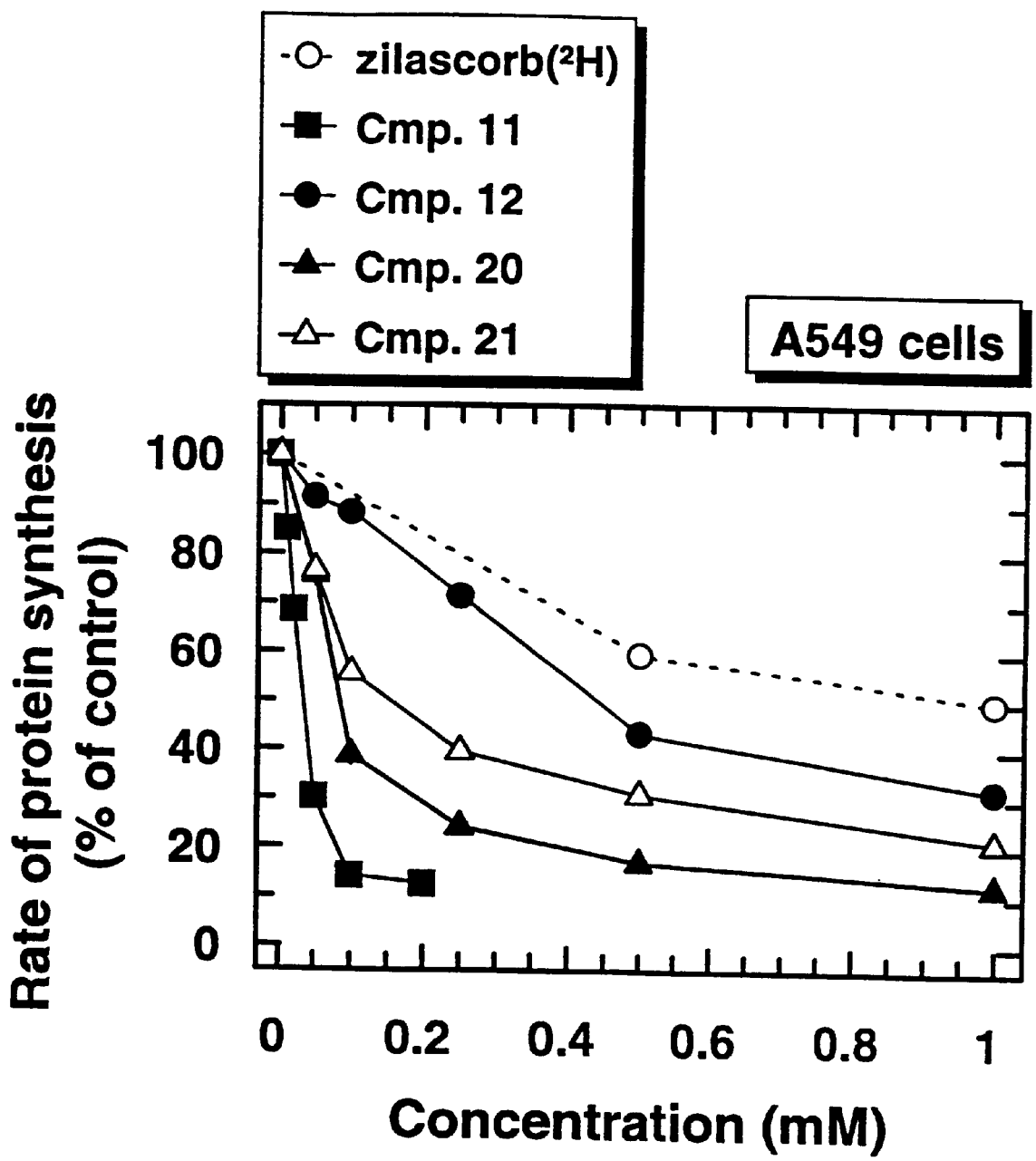

In FIG. 3, the rate of protein synthesis (as % of control rate) is shown in relation to the concentration of 14 different compounds used in the treatment of human A549 lung carcinoma cells cultivated in vitro. The treatment period was for 1 hour during which the cell culture medium contained [$^{3}$H]valine in addition to the test compound. In panel A it is shown that the rate of protein synthesis is inhibited to a far greater degree by treatment with benzylidene-d$_{1}$-diacetate (Compound 2), or either of the two nitrobenzylidene diacetate compounds Compounds 5 and 6 as compared to the effect of the prior art compound zilascorb($^{2}$H).

In panel B of FIG. 3, it is shown that the rate of protein synthesis in human As49 lung carcinoma cells is inhibited to a greater degree by treatment with several substituted benzylidene diacetates (Compound 3, Compound 4, Compound 8, Compound 9) as compared to the effect of the prior art compound zilascorb($^{2}$H).

In panel C of FIG. 3, it is shown that the rate of protein synthesis in human A549 lung carcinoma cells is inhibited to a greater degree by treatment with dioxane derivatives Compound 20 and 21 as compared to the effect of the prior art compound zilascorb($^{2}$H). Additionally, the acetoxy benzylidene compounds Compound 11 and 12 also inhibit protein synthesis to a greater degree than the prior art compound zilascorb($^{2}$H), with Compound 11 being the most active compound.

In panel D of FIG. 3, the effect on protein synthesis in human A549 lung carcinoma cells following treatment with a heterocyclic acetoxy compound is shown. The pyridine compound Compound 19 induced a far greater inhibition of protein synthesis than the prior art compound zilascorb($^{2}$H),.

Figure 4A:
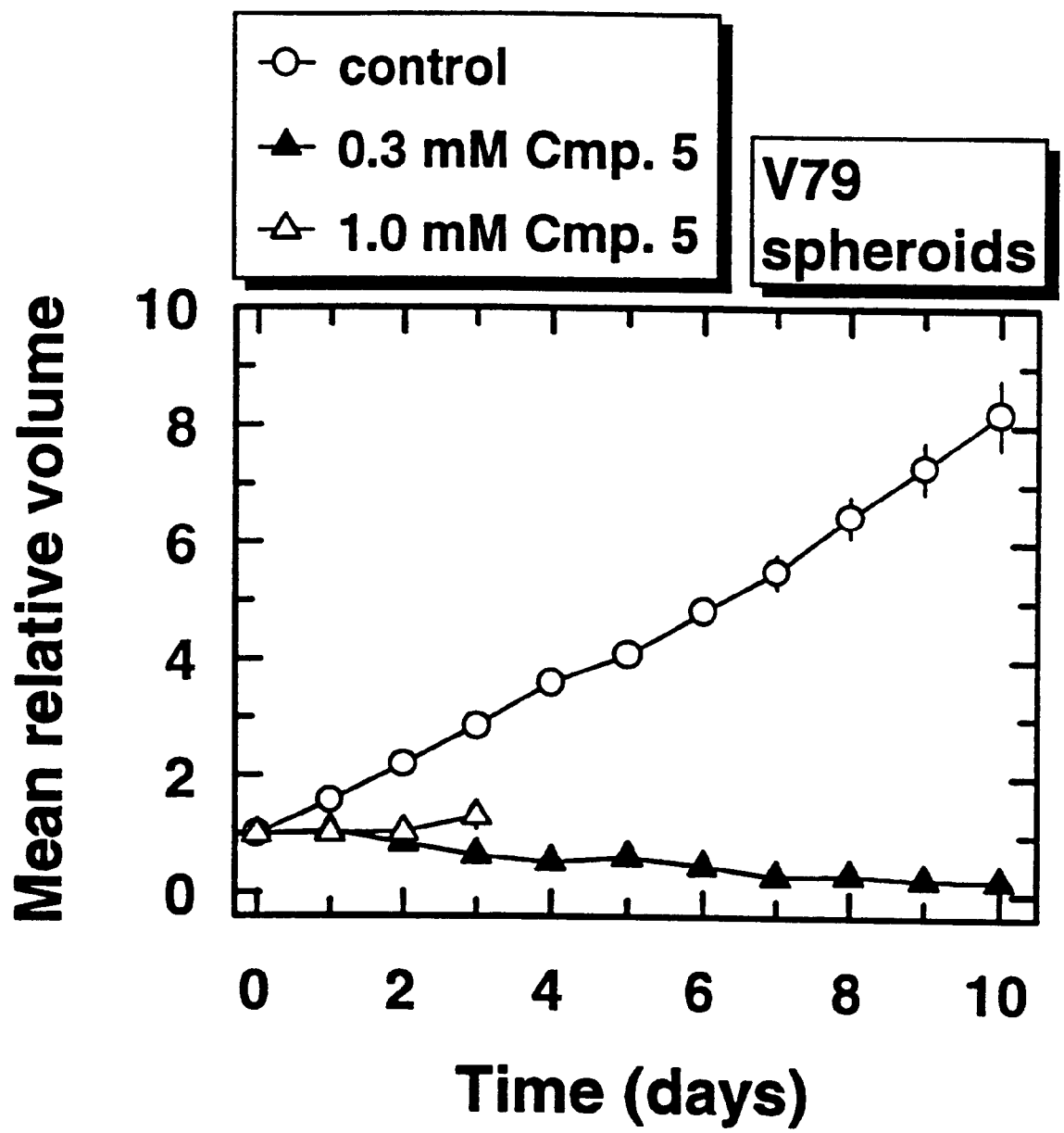
FIGS. 4–6 show the rate of tumor growth in relationship to various compounds.
Figure 4B:
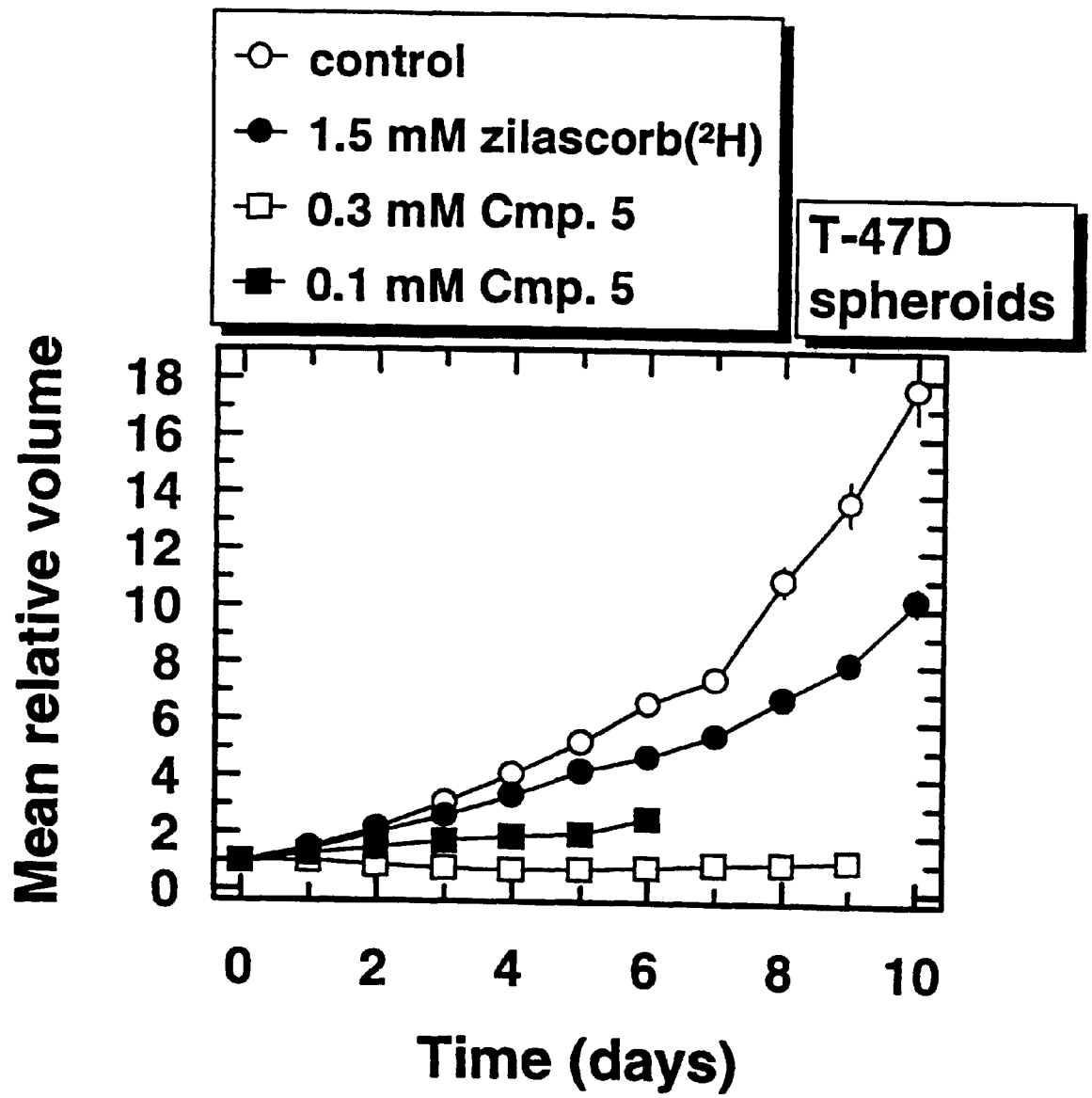
Figure 5A:
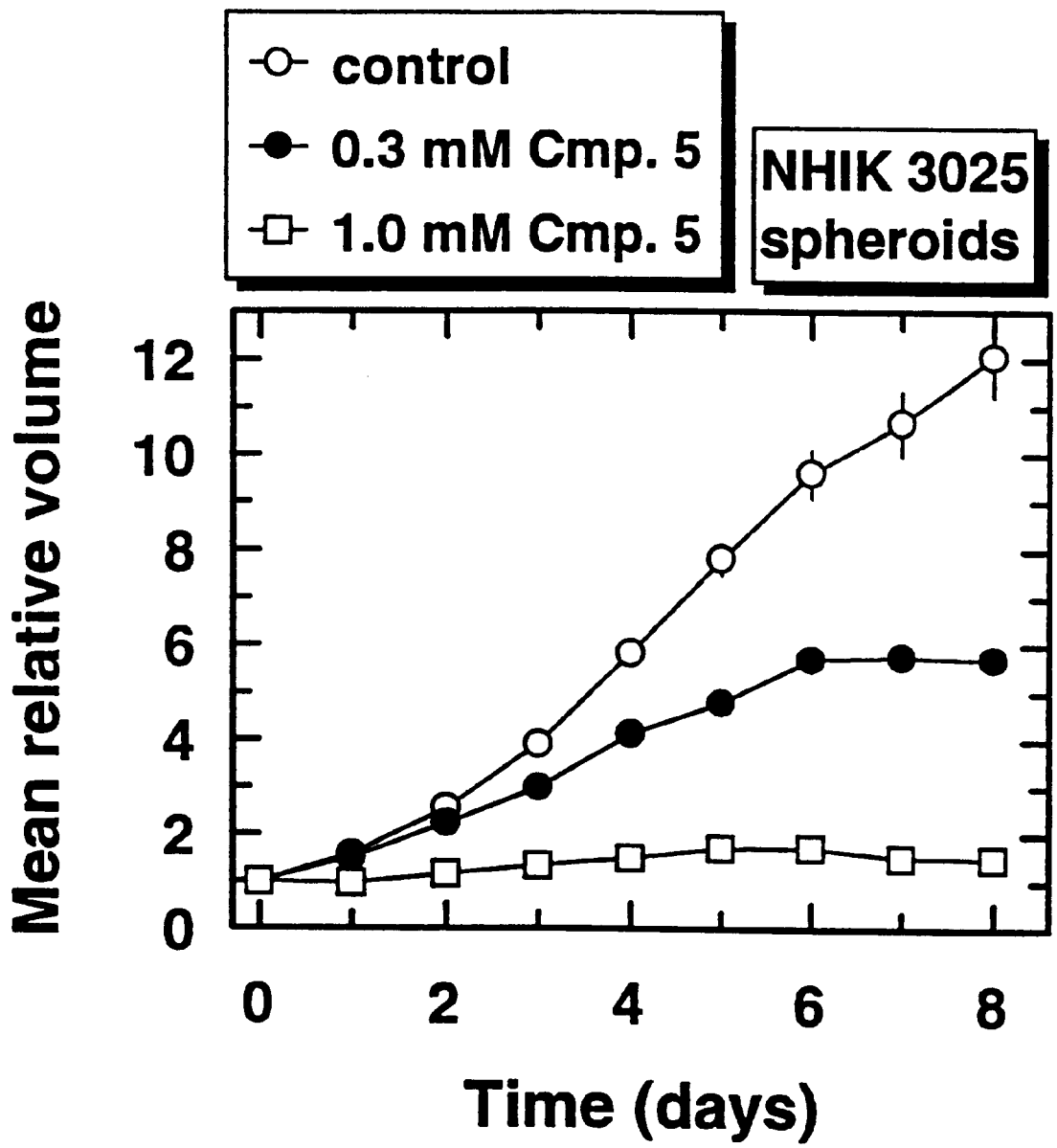

In FIGS. 4 and 5A, the effect of the nitrobenzylidene diacetate Compound 5 on growth of multi-cellular tumor spheroids grown in vitro. From these figures it can be seen that Compound 5 inhibits the growth of spheroids formed from V79 Chinese hamster lung cells, NHIK 3025 human cervix carcinoma cells (FIG. 5A), and T-47D human mammary carcinoma cells (FIG. 4B). Growth of spheroids from all three cell types was inhibited in a dose-dependent manner, with T-47D spheroids being most sensitive to Compound 5.

Figure 5B:
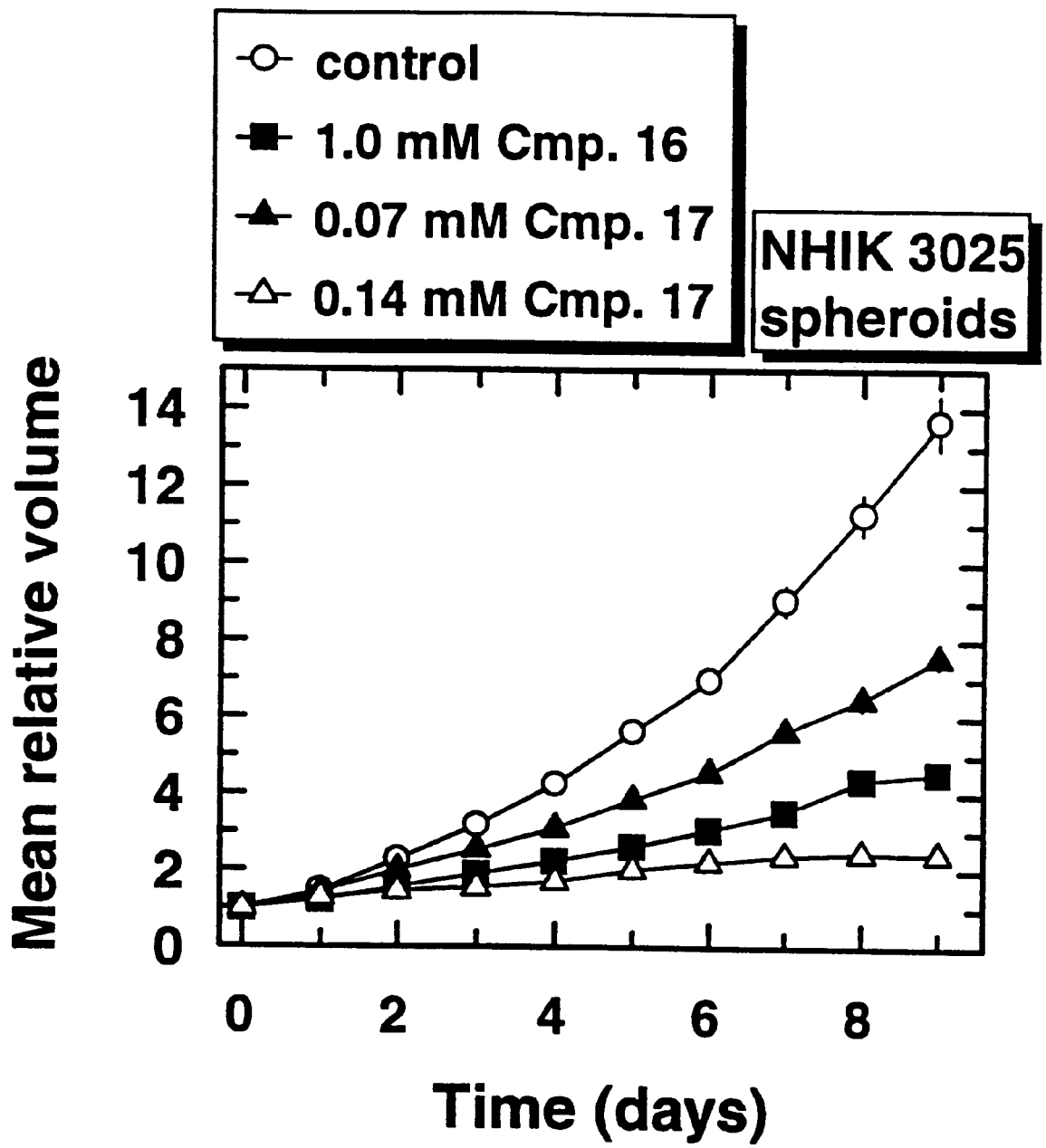

In FIG. 5B shows the effect of compounds 16 and 17 on the growth of multicellar tumor spheroids grown in vitro. From this figure, it can be seen that compounds 16 and 17 inhibit the growth of spheroids formed from NHIK 3025 human cervix carcinoma cells.

Figure 6A:
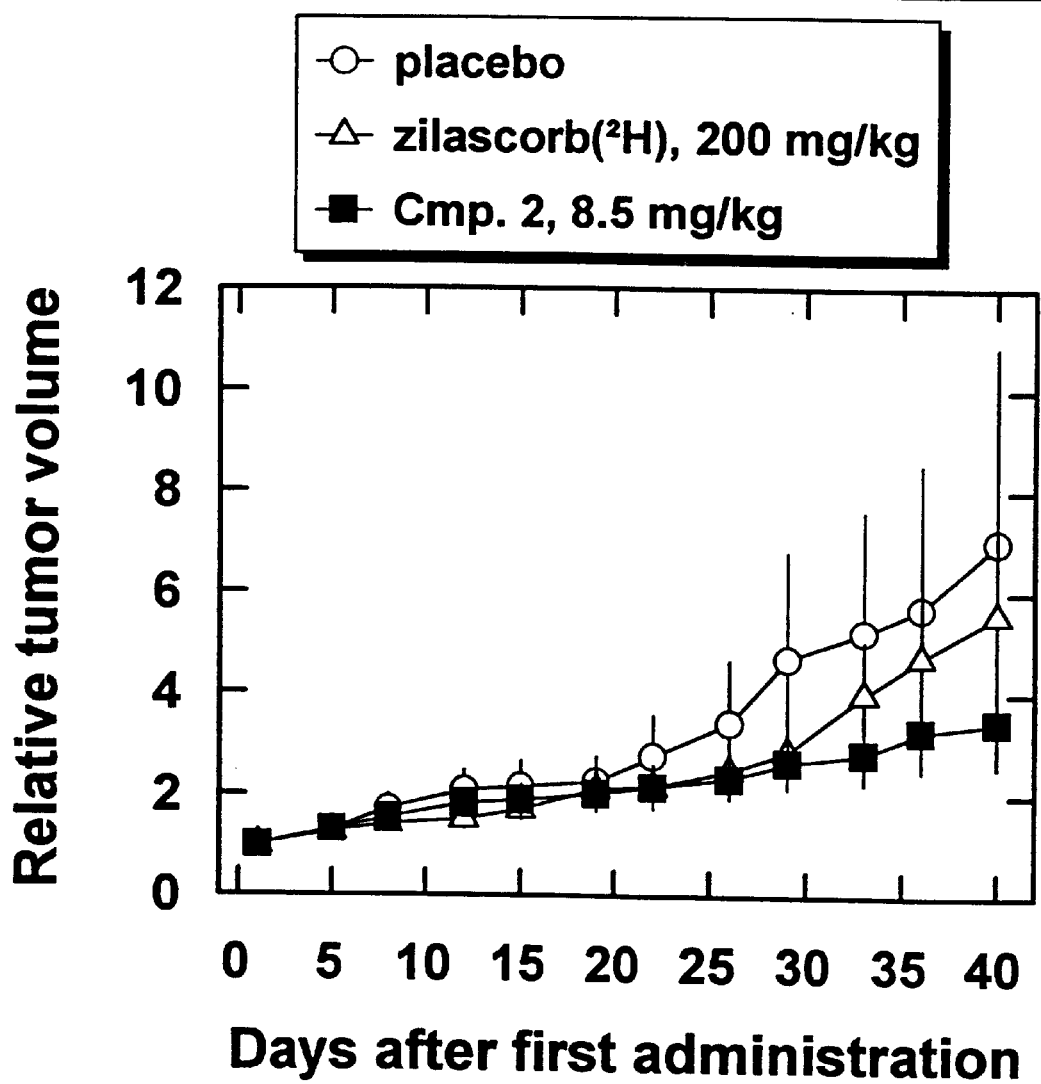
Figure 6B:
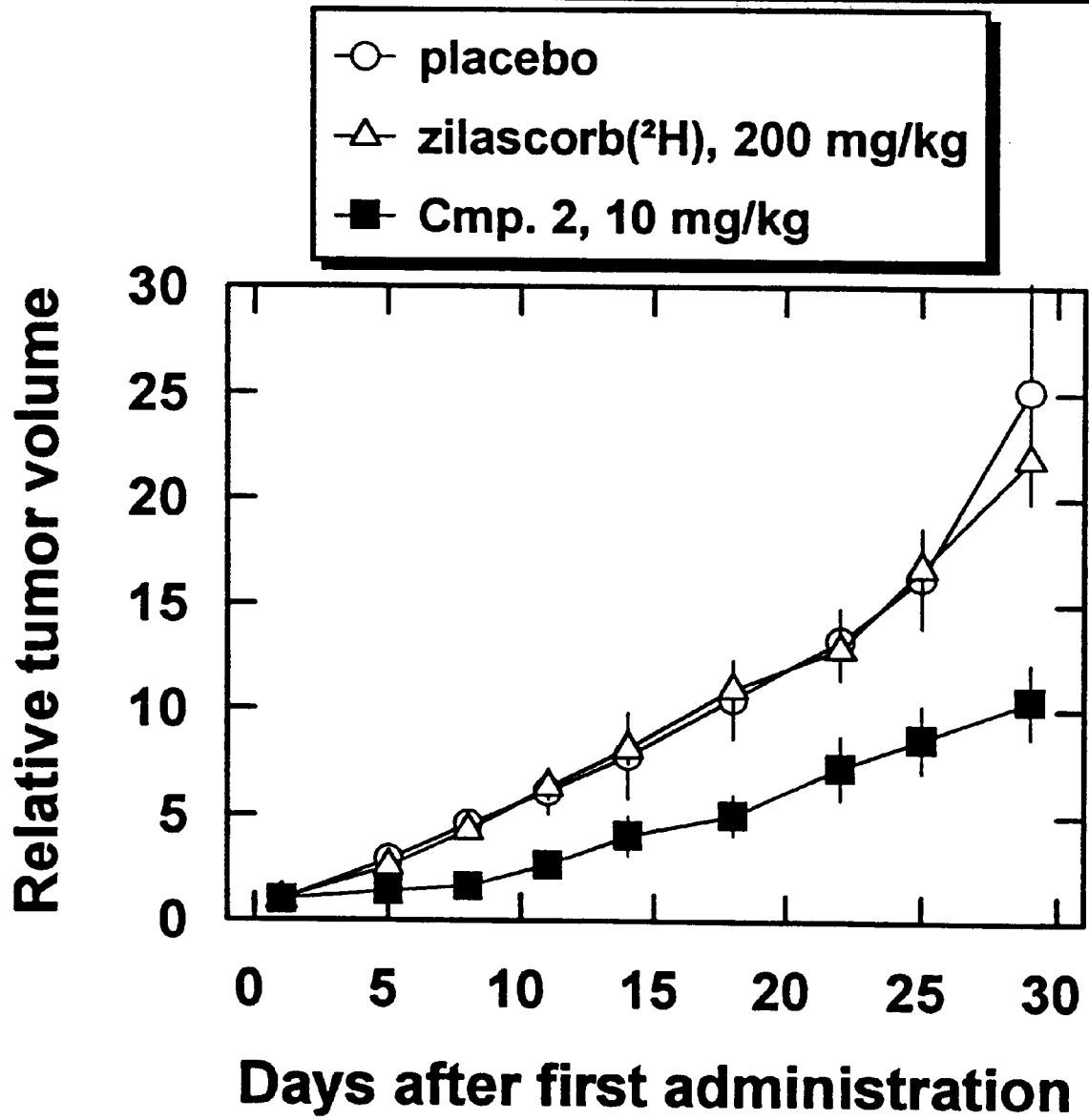

The inhibition of in vivo tumor growth by daily administration of benzylidene-d$_{1}$-diacetate (Compound 2) is shown in FIG. 6. Data in panel A demonstrate that daily oral administration of 8.5 mg/kg benzylidene-d$_{1}$-diacetate (Compound 2) to athymic mice bearing SK-OV human ovarian carcinoma xenografts reduces tumor growth far better than the prior art compound zilascorb($^{2}$H) administered orally at 200 mglkg. Another human tumor tested was A549 lung carcinoma (panel B). Treatment of mice with 10 mg/kg Compound 2 orally each day inhibited tumor growth to a far greater degree than the prior art compound zilascorb ($^{2}$H), which in this tumor type had little effect.

Administration

The pharmaceutical compositions according to the present invention may be administered in anti cancer treatment or in treatment of diseases which arise due to abnormally elevated cell proliferation.

For this purpose the compounds of formula(I) may be formulated in any suitable manner for administration to a patient, either alone or in admixture with suitable pharmaceutical carriers or adjuvants.

It is especially preferred to prepare the formulations for systemic therapy either as oral preparations or parenteral formulations.

Suitable enteral preparations will be tablets, capsules, e.g. soft or hard gelatine capsules, granules, grains or powders, syrups, suspensions, solutions or suppositories. Such will be prepared as known in the art by mixing one or more of the compounds of formula(I) with non-toxic, inert, solid or liquid carriers.

Suitable parental preparations of the compounds of formula(I) are injection or infusion solutions.

When administered topically the compounds of formula (I) may be formulated as a lotion, salve, cream, gel, tincture, spray or the like containing the compounds of formula(I) in admixture with non-toxic, inert, solid or liquid carriers which are usual in topical preparations. It is especially suitable to use a formulation which protects the active ingredient against air, water and the like.

The preparations can contain inert or pharmacodynamically active additives. Tablets or granulates e.g. can contain a series of binding agents, filler materials, carrier substances and/or diluents. Liquid preparations may be present, for example, in the form of a sterile solution. Capsules can contain a filler material or thickening agent in addition to the active ingredient. Furthermore, flavor-improving additives as well as the substances usually used as preserving, stabilizing, moisture-retaining and emulsifying agents, sals for varying the osmotic pressure, buffers and other additives may also be present.

The dosages in which the preparations are administered can vary according to the indication, the mode of use and the route of administration, as well as to the requirements of the patient. In general a daily dosage for a systemic therapy for an adult average patient in need of anticancer treatment will be about 0.1–500 mg/kg body weight/day, preferably 2–200 mg/kg body weight/day.

The daily dosage for a systemic therapy for an adult average patient in need of treatment for elevated cell proliferation will be about 0.1–50 mg/kglday preferably 1–15 mg/kg/day. For topic administration, the suitable salve or ointment can contain from 0.1–50% by weight of the pharmaceutical formulation, especially 1–20%.

If desired the pharmaceutical preparation of the compound of formula(I) can contain an andoxidant, e.g. tocopherol, N-methyl-tocopheramine, butylated hydroxyanisole, ascorbic acid or butylated hydroxytoluene.

We claim:

1. A method of treating a patient afflicted with cancer, said method comprising administering to said patient a therapeutically effective amount of a compound having formula (I)

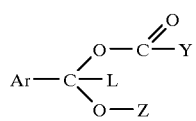

(I)

wherein L is H or D;

Ar is phenyl or a 5- or 6-membered heterocyclic ring, the heteroatom being O, N or S, and wherein Ar may optionally be partly or fully deuterated, or substituted, the optional substituents being the same or different and selected from group consisting of $C_{1-20}$ alkyl, which is branched or linear, fluoroalkyl, $C_{2-20}$ alkenyl which is branched or linear, $C_{2-20}$ alkynyl, which is branched or linear, phenyl, nitrophenyl, halogen, nitro, cyano, amino, mono ($C_{1-20}$) alkylamino, di ($C_{1-20}$) alkylamino wherein the alkyl groups are the same or are different, OR, wherein R is D or $C_{1-20}$ alkyl, CA(OR)$_2$ wherein A is H or D and R is $C_{1-20}$ alkyl or $C_{1-20}$ acyl, COA wherein A is H, D or $C_{1-20}$ alkyl, COOR wherein R is H, D or $C_{1-20}$ alkyl, and CONR$_1$R$_2$ wherein R$_1$ and R$_2$ are the same or are different and each is H, D or $C_{1-20}$ alkyl, Y is H, D, $C_{1-20}$ alkyl, $C_{2-20}$ alkenyl with 1–6 double bonds or $C_{2-20}$ alkynyl with 1–6 triple bonds, and where the alkyl, alkenyl or alkynyl groups may optionally be substituted with $C_{1-20}$ alkyl, phenyl, nitrophenyl, halogen, nitro, cyano, amino, mono($C_{1-20}$) alkylamino or di ($C_{1-20}$) alkylamino wherein the alkyl groups are the same or are different, or Y is:
OR wherein R is H, D or $C_{1-20}$ alkyl,
CA(OR)$_2$ wherein A is H or D and R is $C_{1-20}$ alkyl or $C_{1-20}$ acyl,
COA wherein A is H, D or $C_{1-20}$ alkyl,
COOR wherein R is H, D or $C_{1-20}$ alkyl, and
CONR$_1$R$_2$ wherein R$_1$ and R$_2$ are the same or are different and each is H, D or $C_{1-20}$ alkyl; and Z is Y or COY, wherein Y is as defined above, the Y substituents in the compound of formula (I) being the same or different; or the Z-O-C(Ar)L-O-CO-Y sequence in formula (I) forms a 5- or 6-membered ring where Y and Z comprise a common alkyl chain of 1 or 2 carbon atoms which may optionally be mono- or di-substituted with the same or different substituents which are situated on the same or different carbon atoms and are selected from the group consisting of $C_{1-20}$ alkyl, $C_{2-20}$ alkenyl with 1–6 double bonds and $C_{2-20}$ alkynyl with 1–6 triple bonds, wherein said alkyl, alkenyl or alkynyl optional substituent groups may be optionally substituted with substituents selected from the group consisting of $C_{1-20}$ alkyl, phenyl, nitrophenyl, halogen, nitro, cyano, amino, mono ($C_{1-20}$) alkylamino, di($C_{1-20}$) alkylamino wherein the alkyl groups are the same or different, OR, CA(OR)$_2$, COA, COOR and CONR$_1$R$_2$, wherein OR, CA(OR)$_2$, COA COOR and CONR$_1$R$_2$ are as defined above;

and wherein the Y-Z link may optionally comprise a fused aromatic ring and the aromatic ring may optionally be substituted with $C_{1-20}$ alkyl, phenyl, nitrophenyl, halogen, nitro, cyano, amino, mono($C_{1-20}$) alkylamino, di($C_{1-20}$) alkylamino wherein the alkyl groups are the same or are different, OR, CA(OR)$_2$, COA, COOR and CONR$_1$R$_2$ wherein OR, CA(OR)$_2$, COA, COOR or CONR$_1$R$_2$ are as defined above;

with the proviso that when Y and Z are not connected to form a ring, Ar cannot be an unsubstituted phenyl ring;

and with the further proviso that the compound 5-nitro-2-furfurylidene diacetate is excluded as a compound of formula I or a pharmaceutically acceptable salt of a compound of formula I.

2. The method according to claim 1, wherein Y is CH$_3$ and Z is COCH$_3$.

3. The method according to claim 1, wherein Ar is mono- or di-substituted phenyl, the substituent or substituents of which are the same or different and are selected from the group consisting of CH$_3$, CF$_3$, F, NO$_2$, CN, CO$_2$CH$_3$, CH(OAc)$_2$ and CD(OAc)$_2$.

4. The method according to claim 1 wherein Ar is nitrofuranyl.

5. The method according to claim 1 wherein Ar is phenyl.

6. The method according to claim 1 wherein L is deuterium.

7. The method according to claim 1 wherein the compound of formula (I) is:
3-methylbenzylidene diacetate;
4-methylbenzylidene diacetate;
3-nitrobenzylidene diacetate;
4-nitrobenzylidene diacetate;
4-cyanobenzylidene diacetate;
4-fluorobenzylidene diacetate;
4-carbomethoxybenzylidene diacetate;

4-sodiumcarboxybenzylidene diacetate;
3-diacetoxymethylbenzylidene diacetate;
3-acetoxy-5-ethoxy-benzylidene diacetate;
4-sodiumcarboxybenzylidene dibutanoate;
2-furfurylidene diacetate;
thiophene-2-carboxaldehyde diacetate;
pyridine-3-carboxaldehyde diacetate;
2-(R,S)-phenyl-1,3-dioxolane-4-one; or
(2R,S;5S)-2-phenyl-5-methyl-1,3-dioxolane-4-one.

8. A method for treating a patient afflicted with an illness arising from abnormally elevated cell proliferation, said method comprising administering to said patient a therapeutically effective amount of a compound having formula (I)

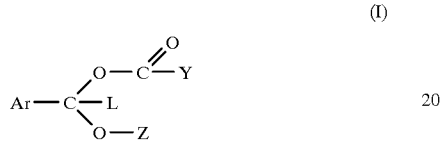

wherein L is H or D;

Ar is phenyl or a 5- or 6-membered heterocyclic ring, the heteroatom being O, N or S, and wherein Ar may optionally be partly or fully deuterated, or substituted, the optional substituents being the same or different and selected from group consisting of $C_{1-20}$ alkyl, which is branched or linear, fluoroalkyl, $C_{2-20}$ alkenyl which is branched or linear, $C_{2-20}$ alkynyl, which is branched or linear, phenyl, nitrophenyl, halogen, nitro, cyano, amino, mono $(C_{1-20})$ alkylamino, di $(C_{1-20})$ alkylamino wherein the alkyl groups are the same or are different, OR, wherein R is D or $C_{1-20}$ alkyl, $CA(OR)_2$ wherein A is H or D and R is $C_{1-20}$ alkyl or $C_{1-20}$ acyl, COA wherein A is H, D or $C_{1-20}$ alkyl, COOR wherein R is H, D or $C_{1-20}$ alkyl, and $CONR_1R_2$ wherein $R_1$ and $R_2$ are the same or are different and each is H, D or $C_{1-20}$ alkyl, Y is H, D, $C_{1-20}$ alkyl, $C_{2-20}$ alkenyl with 1–6 double bonds or $C_{2-20}$ alkynyl with 1–6 triple bonds, and where the alkyl, alkenyl or alkynyl groups may optionally be substituted with $C_{1-20}$ alkyl, phenyl, nitrophenyl, halogen, nitro, cyano, amino, mono$(C_{1-20})$ alkylamino or di $(C_{1-20})$ alkylamino wherein the alkyl groups are the same or are different, or Y is:
OR wherein R is H, D or $C_{1-20}$ alkyl,
$CA(OR)_2$ wherein A is H or D and R is $C_{1-20}$ alkyl or $C_{1-20}$ acyl,
COA wherein A is H, D or $C_{1-20}$ alkyl,
COOR wherein R is H, D or $C_{1-20}$ alkyl, and
$CONR_1R_2$ wherein $R_1$ and $R_2$ are the same or are different and each is H, D or $C_{1-20}$ alkyl; and Z is Y or COY, wherein Y is as defined above, the Y substituents in the compound of formula (I) being the same or different; or the Z-O-C(Ar)L-O-CO-Y sequence in formula (I) forms a 5- or 6-membered ring where Y and Z comprise a common alkyl chain of 1 or 2 carbon atoms which may optionally be mono- or di-substituted with the same or different substituents which are situated on the same or different carbon atoms and are selected from the group consisting of $C_{1-20}$ alkyl, $C_{2-20}$ alkenyl with 1–6 double bonds and $C_{2-20}$ alkynyl with 1–6 triple bonds, wherein said alkyl, alkenyl or alkynyl optional substituent groups may be optionally substituted with substituents selected from the group consisting of $C_{1-20}$ alkyl, phenyl, nitrophenyl, halogen, nitro, cyano, amino, mono $(C_{1-20})$ alkylamino, di$(C_{1-20})$ alkylamino wherein the alkyl groups are the same or different, OR, $CA(OR)_2$, COA, COOR and $CONR_1R_2$, wherein OR, $CA(OR)_2$, COA COOR and $CONR_1R_2$ are as defined above;

and wherein the Y-Z link may optionally comprise a fused aromatic ring and the aromatic ring may optionally be substituted with $C_{1-20}$ alkyl, phenyl, nitrophenyl, halogen, nitro, cyano, amino, mono$(C_{1-20})$ alkylamino, di$(C_{1-20})$ alkylamino wherein the alkyl groups are the same or are different, OR, $CA(OR)_2$, COA, COOR and $CONR_1R_2$ wherein OR, $CA(OR)_2$, COA, COOR or $CONR_1R_2$ are as defined above;

with the proviso that when Y and Z are not connected to form a ring, Ar cannot be an unsubstituted phenyl ring;

and with the further proviso that the compound 5-nitro-2-furfurylidene diacetate is excluded as a compound of formula 1, or a pharmaceutically acceptable salt of a compound of formula I.

9. The method according to claim 8, wherein Y is $CH_3$ and Z is $COCH_3$.

10. The method according to claim 8, wherein Ar is mono- or di-substituted phenyl, the substituent or substituents of which are the same or different and are selected from the group consisting of $CH_3$, $CF_3$, F, $NO_2$, CN, $CO_2CH_3$, $CH(OAc)_2$ and $CD(OAc)_2$.

11. The method according to claim 8 wherein Ar is nitrofuranyl.

12. The method according to claim 8 wherein Ar is phenyl.

13. The method according to claim 8 wherein L is deuterium.

14. The method according to claim 8 wherein the compound of formula (I) is:

3-methylbenzylidene diacetate;
4-methylbenzylidene diacetate;
3-nitrobenzylidene diacetate;
4-nitrobenzylidene diacetate;
4-cyanobenzylidene diacetate;
4-fluorobenzylidene diacetate;
4-carbomethoxybenzylidene diacetate;
4-sodiumcarboxybenzylidene diacetate;
3-diacetoxymethylbenzylidene diacetate;
3-acetoxy-5-ethoxy-benzylidene diacetate;
4-sodiumcarboxybenzylidene dibutanoate;
2-furfurylidene diacetate;
thiophene-2-carboxaldehyde diacetate;
pyridine-3-carboxaldehyde diacetate;
2-(R,S)-phenyl-1,3-dioxolane-4-one; or
(2R,S;5S)-2-phenyl-5-methyl-1,3-dioxolane-4-one.

15. A pharmaceutical composition comprising (a) a pharmaceutically effective amount of compound of formula (I):

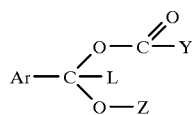
(I)

wherein L is deuterium;

Ar is phenyl or a 5- or 6-membered heterocyclic ring, the heteroatom being O, N or S, and wherein Ar may optionally be partly or fully deuterated, or substituted, the optional substituents being the same or different and selected from group consisting of $C_{1-20}$ alkyl, which is branched or linear, fluoroalkyl, $C_{2-20}$ alkenyl which is branched or linear, $C_{2-20}$ alkynyl, which is branched or linear, phenyl, nitrophenyl, halogen, nitro, cyano, amino, mono ($C_{1-20}$) alkylamino, di ($C_{1-20}$) alkylamino wherein the alkyl groups are the same or are different, OR, wherein R is D or $C_{1-20}$ alkyl, $CA(OR)_2$ wherein A is H or D and R is $C_{1-20}$ alkyl or $C_{1-20}$ acyl, COA wherein A is H, D or $C_{1-20}$ alkyl, COOR wherein R is H, D or $C_{1-20}$ alkyl, and $CONR_1R_2$ wherein $R_1$ and $R_2$ are the same or are different and each is H, D or $C_{1-20}$ alkyl, Y is H, D, $C_{1-20}$ alkyl, $C_{2-20}$ alkenyl with 1–6 double bonds or $C_{2-20}$ alkynyl with 1–6 triple bonds, and where the alkyl, alkenyl or alkynyl groups may optionally be substituted with $C_{1-20}$ alkyl, phenyl, nitrophenyl, halogen, nitro, cyano, amino, mono($C_{1-20}$) alkylamino or di ($C_{1-20}$) alkylamino wherein the alkyl groups are the same or are different, or Y is:

OR wherein R is H, D or $C_{1-20}$ alkyl, $CA(OR)_2$ wherein A is H or D and R is $C_{1-20}$ alkyl or $C_{1-20}$ acyl, COA wherein A is H, D or $C_{1-20}$ alkyl, COOR wherein R is H, D or $C_{1-20}$ alky, and $CONR_1R_2$ wherein $R_1$ and $R_2$ are the same or are different and each is H, D or $C_{1-20}$ alkyl; and Z is Y or COY, wherein Y is as defined above, the Y substituents in the compound of formula (I) being the same or different; or the Z-O-C(Ar)L-O-CO-Y sequence in formula (I) forms a 5- or 6-membered ring where Y and Z comprise a common alkyl chain of 1 or 2 carbon atoms which may optionally be mono- or di-substituted with the same or different substituents which are situated on the same or different carbon atoms and are selected from the group consisting of $C_{1-20}$ alkyl, $C_{2-20}$ alkenyl with 1–6 double bonds and $C_{2-20}$ alkynyl with 1–6 triple bonds, wherein said alkyl, alkenyl or alkynyl optional substituent groups may be optionally substituted with substituents selected from the group consisting of $C_{1-20}$ alkyl, phenyl, nitrophenyl, halogen, nitro, cyano, amino, mono ($C_{1-20}$) alkylamino, di ($C_{1-20}$) alkylamino wherein the alkyl groups are the same or different, OR, $CA(OR)_2$, COA, COOR and $CONR_1R_2$, wherein OR, $CA(OR)_2$, COA COOR and $CONR_1R_2$ are as defined above;

and wherein the Y-Z link may optionally comprise a fused aromatic ring and the aromatic ring may optionally be substituted with $C_{1-20}$ alkyl, phenyl, nitrophenyl, halogen, nitro, cyano, amino, mono($C_{1-20}$) alkylamino, di($C_{1-20}$) alkylamino wherein the alkyl groups are the same or are different, OR, $CA(OR)_2$, COA, COOR and $CONR_1R_2$ wherein OR, $CA(OR)_2$, COA, COOR or $CONR_1R_2$ are as defined above;

with the proviso that when Y and Z are not connected to form a ring, Ar cannot be an unsubstituted phenyl ring;

and with the further proviso that the compound 5-nitrofurfurylidene diacetate is excluded as a compound of formula I;

or a pharmaceutically acceptable salt of a compound of formula I; and (b) a pharmaceutically acceptable carrier or adjuvant, therefor.

16. The pharmaceutical composition according to claim 15, wherein Y is $CH_3$ and Z is $COCH_3$.

* * * * *